United States Patent
Diodone et al.

(10) Patent No.: US 10,221,125 B2
(45) Date of Patent: Mar. 5, 2019

(54) SOLID FORMS

(71) Applicant: Oryzon Genomics, S.A., Madrid (ES)

(72) Inventors: Ralph Diodone, Breisach (DE); Urs Schwitter, Reinach BL (CH); René Trussardi, Birsfelden (CH)

(73) Assignee: Oryzon Genomics, S.A., Madrid (ES)

( * ) Notice: Subject to any disclaimer, the term of this patent is extended or adjusted under 35 U.S.C. 154(b) by 0 days.

(21) Appl. No.: 15/571,945

(22) PCT Filed: May 2, 2016

(86) PCT No.: PCT/EP2016/059726
§ 371 (c)(1),
(2) Date: Nov. 6, 2017

(87) PCT Pub. No.: WO2016/177656
PCT Pub. Date: Nov. 10, 2016

(65) Prior Publication Data
US 2018/0086692 A1    Mar. 29, 2018

(30) Foreign Application Priority Data
May 6, 2015    (EP) .................................. 15166641

(51) Int. Cl.
| | | |
|---|---|---|
| *C07C 211/40* | (2006.01) | |
| *C07C 209/62* | (2006.01) | |
| *C07D 209/84* | (2006.01) | |
| *C07C 209/84* | (2006.01) | |

(52) U.S. Cl.
CPC .......... *C07C 211/40* (2013.01); *C07C 209/62* (2013.01); *C07C 209/84* (2013.01); *C07B 2200/13* (2013.01); *C07C 2601/02* (2017.05); *C07C 2601/14* (2017.05)

(58) Field of Classification Search
CPC .... C07C 211/40; C07C 209/62; C07C 209/84
See application file for complete search history.

(56) References Cited

U.S. PATENT DOCUMENTS

| | | | |
|---|---|---|---|
| 8,524,717 B2 | 9/2013 | Guibourt et al. | |
| 8,722,743 B2 | 5/2014 | Ortega-Munoz et al. | |
| 8,859,555 B2 | 10/2014 | Ortega-Muñoz et al. | |
| 8,946,296 B2 | 2/2015 | Ortega Muñoz et al. | |
| 8,993,808 B2 | 3/2015 | Guibourt et al. | |
| 9,006,449 B2 | 4/2015 | Fyfe et al. | |
| 9,061,966 B2 | 6/2015 | Laria et al. | |
| 9,149,447 B2 | 10/2015 | Ortega-Muñoz et al. | |
| 9,181,198 B2 | 11/2015 | Ortega-Muñoz et al. | |
| 9,186,337 B2 | 11/2015 | Baker et al. | |
| 9,469,597 B2* | 10/2016 | Ortega Munoz | C07C 271/24 |
| 9,487,512 B2 | 11/2016 | Ortega Muñoz et al. | |
| 9,616,058 B2 | 4/2017 | Cesar Castro Palomino Laria et al. | |
| 9,670,136 B2* | 6/2017 | Ortega Munoz | C07C 271/24 |
| 9,676,701 B2 | 6/2017 | Fyfe et al. | |
| 9,708,309 B2 | 7/2017 | Ortega-Muñoz et al. | |
| 9,790,196 B2 | 10/2017 | Baker et al. | |
| 9,908,859 B2 | 3/2018 | Baker et al. | |
| 9,944,601 B2 | 4/2018 | Ortega-Muñoz et al. | |
| 2008/0139665 A1 | 6/2008 | Schuele et al. | |
| 2010/0324147 A1 | 12/2010 | McCafferty et al. | |
| 2014/0296255 A1 | 10/2014 | Maes et al. | |
| 2014/0329833 A1 | 11/2014 | Maes et al. | |
| 2015/0368186 A1 | 12/2015 | Ortega Muñoz et al. | |
| 2016/0000768 A1 | 1/2016 | Castro-Palomino Laria et al. | |
| 2016/0045456 A1 | 2/2016 | Guibourt et al. | |
| 2016/0081947 A1 | 3/2016 | Maes et al. | |
| 2017/0209432 A1 | 7/2017 | Fyfe et al. | |
| 2017/0281566 A1 | 10/2017 | Ciceri et al. | |
| 2017/0281567 A1 | 10/2017 | Demario et al. | |
| 2018/0079709 A1 | 3/2018 | Ortega Muñoz et al. | |
| 2018/0127406 A1 | 5/2018 | Ortega-Muñoz et al. | |

FOREIGN PATENT DOCUMENTS

| | | |
|---|---|---|
| EP | 1704859 | 9/2006 |
| WO | WO2006/071608 | 7/2006 |
| WO | WO2006/087206 | 8/2006 |
| WO | WO2007/021839 | 7/2007 |
| WO | WO2008/127734 | 10/2008 |
| WO | WO2010/011845 | 1/2010 |

(Continued)

OTHER PUBLICATIONS

Voskoglou-Nomikos et al., Clinical Cancer Research, vol. 9, 4227-4239, 2003.*
ptcl.chem.ox.ac.uk/MSDS structure activity relationship; Jaworska, 1-8, 2004.*
Cancer and Metastasis Reviews (1998), 17(1), 91-106.*
Science (1999), vol. 286, 531-537.*
Caira, Mino R., "Crystalline Polymorphism of Organic Compounds," Topics in Current Chemistry, vol. 198, pp. 163-208 (1998).
International Search Report for International Application No. PCT/EP2016/059726, Aug. 8, 2016.
Written Opinion of the International Searching Authority for International Application No. PCT/EP2016/059726.

(Continued)

*Primary Examiner* — Rebecca L Anderson
(74) *Attorney, Agent, or Firm* — Finnegan, Henderson, Farabow, Garrett & Dunner, LLP

(57) ABSTRACT

The instant invention relates to novel solid forms of the compound of formula (I) or salts thereof

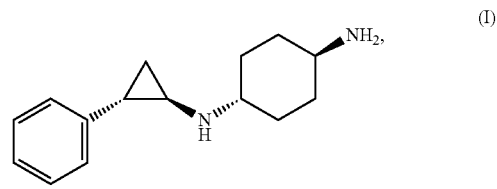
(I)

as well as processes for their manufacture, pharmaceutical compositions comprising them, and their use as medicaments.

34 Claims, 12 Drawing Sheets

(56) References Cited

FOREIGN PATENT DOCUMENTS

| | | |
|---|---|---|
| WO | WO2010/043721 | 4/2010 |
| WO | WO2010/084160 | 7/2010 |
| WO | WO2010/139784 | 12/2010 |
| WO | WO2010/143582 | 12/2010 |
| WO | WO2011/022489 | 2/2011 |
| WO | WO2011/035941 | 3/2011 |
| WO | WO2011/042217 | 4/2011 |
| WO | WO2011/106105 | 9/2011 |
| WO | WO2011/106106 | 9/2011 |
| WO | WO2011/113005 | 9/2011 |
| WO | WO2011/131576 | 10/2011 |
| WO | WO2011/131697 | 10/2011 |
| WO | WO2012/013727 | 2/2012 |
| WO | WO2012/013728 | 2/2012 |
| WO | WO2012/034116 | 3/2012 |
| WO | WO2012/042042 | 4/2012 |
| WO | WO2012/045883 | 4/2012 |
| WO | WO2012/072713 | 6/2012 |
| WO | WO2012/107498 | 8/2012 |
| WO | WO2012/107499 | 8/2012 |
| WO | WO2012/135113 | 10/2012 |
| WO | WO2012/156531 | 11/2012 |
| WO | WO2012/156537 | 11/2012 |
| WO | WO2013/057320 | 4/2013 |
| WO | WO 2013/057322 A1 | 4/2013 |
| WO | WO2016/177656 | 11/2016 |
| WO | WO2016/198649 | 12/2016 |
| WO | WO2017/013061 | 1/2017 |
| WO | WO2017/060319 | 4/2017 |
| WO | WO2017/157813 | 9/2017 |
| WO | WO2017/157825 | 9/2017 |
| WO | WO2017/158136 | 9/2017 |
| WO | WO2017/212061 | 12/2017 |
| WO | WO2018/083138 | 5/2018 |
| WO | WO2018/083189 | 5/2018 |

OTHER PUBLICATIONS

Barlesi et al, "Global histone modifications predict prognosis of resected non small-cell lung cancer",J Clin Oncol,2007,25, 4358-4364.

Benelkebir et al, "Enantioselective synthesis of tranylcypromine analogues as lysine demethylase (LSD1) inhibitors", Bioorg Med Chem, 2011,19(12),3709-3716.

Binda et al, "Biochemical, structural, and biological evaluation of tranylcypromine derivatives as inhibitors of histone demethylases LSD1 and LSD2", J Am Chem Soc,2010,132(19),6827-6833.

Choi et al "Histone demethylase LSD1 is required to induce skeletal muscle differentiation by regulating myogenic factors" (2010) Biochemical and Biophysical Research Communications 401(3), 327-332.

Culhane et al, A mechanism-based inactivator for histone demethylase LSD1, J Am Chem Soc, 2006, 128(14), 4536-4537.

Culhane et al, "Comparative analysis of small molecules and histone substrate analogues as LSD1 lysine demethylase inhibitors", J Am Chem Soc, 2010,132(9),3164-3176.

Di Stefano et al, Mutation of *Drosophila* Lsd1 disrupts H3-K4 methylation, resulting in tissue-specific defects during development, Curr Biol,2007, 17(9), 808-12.

Elsheikh et al "Global histone modifications in breast cancer correlate with tumor phenotypes, prognostic factors and patient outcome", Canc Res, 2009,69, 3802-3809.

Fischer et al, "Recovery of learning and memory is associated with chromatin remodelling", Nature, 2007,447, 178-182.

Forneris et al "LSD1: oxidative chemistry for multifaceted functions in chromatin Regulation." Trends in Biochemical Sciences 2008,33(4), 181-189.

Gooden et al, "Facile synthesis of substituted trans-2-arylcyclopropylamine inhibitors of the human histone demethylase LSD1 and monoamine oxidases A and B", Bioorg Med Chem Lett 2008, 18(10), 3047-51.

Hayami et al, "Overexpression of LSD1 contributes to human carcinogenesis through chromatin regulation in various cancers", Int J Cancer, 2011, 128(3), 574-86.

Huang et al, "Novel oligoamine analogues inhibit lysine-specific demethylase 1 (LSD1) and induce re-expression of epigeneticall silenced genes",Clin Cancer Res,2009, 15(23), 7217-28.

Huang et al, "p53 is regulated by the lysine demethylase LSD1",Nature,2007,449, 105-108.

Huang et al,"Inhibition of lysine-specific demethylase 1 by polyamine analogues results in reexpression of aberrantly silenced genes", PNAS,2007, 104(19), 8023-8028.

Kahl et al, Androgen receptor coactivators lysine-specific histone demethylase 1 and four and a half LIM domain protein 2 predict risk of prostate cancer recurrence, Cancer Res,2006,66 (23), 11341-11347.

Lan et al "Mechanisms involved in the regulation of histone lysine demethylases". Current Opinion in Cell Biology, 2008,20, 316-325.

Lee et al, "Histone H3 lysine 4 demethylation is a target of nonselective antidepressive medications",Chem Biol, 2006,13(6), 563-567.

Liang et al, "Inhibition of the histone demethylase LSD1 blocks alpha-herpesvirus lytic replication and reactivation from latency",Nat Med, 2009,15 (11), 1312-1317.

Lim et al, "Lysine-specific demethylase 1 (LSD1) is highly expressed in ER-negative breast cancers and a biomarker predicting aggressive biology", Carcinogenesis,2010, 31(3), 512-20.

Metzger et al, "LSD1 demethylates repressive histone marks to promote androgen-receptor-dependent transcription",Nature,2005, 437(7057),436-9.

Mimasu et al "Crystal structure of histone demethylase LSD1 and tranylcypromine at 2.25 A" Biochemical and Biophysical Research Communications ,2008,366, 15-22.

Mimasu et al, "Structurally designed trans-2-phenylcyclopropylamine derivatives potently inhibit histone demethylase LSD1/KDM1", Biochemistry,2010,49(30), 6494-6503.

Neelamegan et al, "Brain-penetrant LSD1 inhibitors can block memory consolidation", ACS Chem Neurosci, 2012, 3(2), 120-128.

Ogasawara et al, "Synthesis and biological activity of optically active NCL-1, a lysine-specific demethylase 1 selective inhibitor",Bioorg Med Chem, 2011, doi:10.1016/j.bmc.2010.12.024.

Pollock et al, Lysine-specific histone demethylase 1 inhibitors control breast cancer proliferation in ERalpha-dependent and -independent manners, ACS Chem Biol 2012,7,1221-1231.

Reddy et al, "Role of lysine-specific demethylase 1 in the proinflammatory phenotype of vascular smooth muscle cells of diabetic mice",Circ Res,2008,103, 615-23.

Schmidt et al,"Trans-2-phenylcyclopropylamine is a mechanism-based inactivator of the histone demethylase LSD1", Biochemistry, 2007,46(14),4408-4416.

Schulte et al, "Lysine-specific demethylase 1 is strongly expressed in poorly differentiated neuroblastoma: implications for therapy", Cancer Res,2009,69(5),2065-71.

Scoumanne et al "Protein methylation: a new mechanism of p53 tumor suppressor regulation" Histol Histopathol 2008,23, 1143-1149.

Scoumanne et al, "The lysine-specific demethylase 1 is required for cell proliferation in both p53-dependent and -independent manners", J Biol Chem, 2007,282(21), 15471-5.

Seligson et al, "Global histone modification patterns predict risk of prostate cancer recurrence",Nature, 2005,435, 1262-1266.

Seligson et al,"Global levels of histone modifications predict prognosis in different cancers" ,Am J Path, 2009,174,1619-28.

Sharma et al, "(Bis)urea and (bis)thiourea inhibitors of lysine-specific demethylase 1 as epigenetic modulators", J Med Chem, 2010,53(14), 5197-5212.

Shi et al,"Histone demethylation mediated by the nuclear amine oxidase homolog LSD1", Cell, 2004,119,941-953.

Shi, "Histone lysine demethylases: emerging roles in development, physiology and disease", Nature Reviews Genetics 2007, 8:829-833.

Szewczuk et al, "Mechanistic analysis of a suicide inactivator of histone demethylase LSD1", Biochemistry, 2007,46, 6892-6902.

(56) References Cited

OTHER PUBLICATIONS

Ueda et al, "Identification of cell-active lysine specific demethylase 1-selective inhibitors", J Am Chem Soc, 2009,131(48), 17536-17537.

Wang et al, "Novel histone demethylase LSD1 inhibitors selectively target cancer cells with pluripotent stem cell properties," Cancer Research, 2011, 71(23):7238-49.

Wang et al "LSD1 Is a Subunit of the NuRD Complex and Targets the Metastasis Programs in Breast Cancer" Cell 2009, 138, 660-672.

Wang et al, "The lysine demethylase LSD1 (KDM1) is required for maintenance of global DNA methylation", Nature Genetics, 2009, 41(1), 125-129.

Yang et al "Structural Basis for the Inhibition of the LSD1 Histone Demethylase by the Antidepressant trans-2-Phenylcyclopropylamine" Biochemistry 2007,46 (27), 8058-8065.

Yang et al "Structural basis of histone demethylation by LSD1 revealed by suicide inactivation" Nature Structural & Molecular Biology 2007, 14(6), 535-539.

Johnson et al, CAPLUS, Document No. 157:576967, "Preparation of cyclopropylamines as LSD1 inhibitors in the treatment of cancer", 2012.

Giron et al "Solid state of pharmaceutical compounds. Impact of the ICH Q6 Guideline on industrial development". Journal Thermal Analysis and Calorimetry, 2004, 77:709-747.

Burger and Ramberger. "On the polymorphism of pharmaceuticals and other molecular crystals. I. Theory of thermodynamic rules". Mikrochimica Acta, 1979, 2, 259-271.

Co-pending U.S. Appl. No. 14/843,095, filed Sep. 2, 2015.
Co-pending U.S. Appl. No. 15/458,636, filed Mar. 14, 2017.
Co-pending U.S. Appl. No. 15/458,640, filed Mar. 14, 2017.
Co-pending U.S. Appl. No. 15/497,556, filed Apr. 26, 2017.
Co-pending U.S. Appl. No. 15/623,866, filed Jun. 15, 2017.
Co-pending U.S. Appl. No. 15/735,377, filed Dec. 11, 2017.
Co-pending U.S. Appl. No. 15/741,871, filed Jan. 4, 2018.
Co-pending U.S. Appl. No. 15/766,086, filed Apr. 5, 2018.
Co-pending U.S. Appl. No. 15/911,535, filed Mar. 5, 2018.
Co-pending U.S. Appl. No. 15/988,274, filed May 24, 2018.

\* cited by examiner a)

b)

c)

d)

e)

f)

SOLID FORMS

This application is a national stage filing under 35 U.S.C. § 371 of International Application No. PCT/EP2016/059726, filed on May 2, 2016, which claims priority of European Patent Application No. 15166641.9, filed May 6, 2015. The contents of these applications are each incorporated herein by reference.

The instant invention relates to novel solid forms of the compound of formula (I) or salts thereof

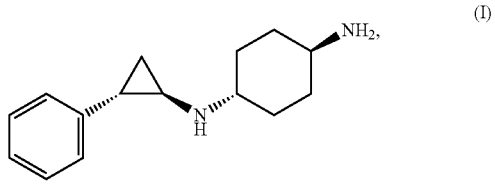 [SMILES: N[C@H]1CC[C@H](N[C@@H]2C[C@H]2c2ccccc2)CC1]

as well as processes for their manufacture, pharmaceutical compositions comprising these solid forms, and their use as medicaments.

BACKGROUND OF THE INVENTION

Polymorphism is the ability of a compound to crystallize as more than one distinct crystal species. Different polymorphic forms (or polymorphs) have different arrangements or conformations of the molecules in the crystal lattice. If a solid does not possess a distinguishable crystal lattice and the molecular arrangement of molecules is disordered, it is considered amorphous. The amorphous state is structurally similar to the liquid state [W. McCrone, *Phys. Chem. Org. Solid State* (1965) 2:725767].

Polymorphic forms of a drug substance can have different chemical, physical and physicotechnical properties. Differences can result from e.g. packing of molecules in the crystal structure (density, refractive index, conductivity, hygroscopicity), thermodynamic properties (melting point, heat capacity, vapor pressure, solubility), kinetic properties (dissolution rate, stability), surface properties (surface free energy, interfacial tension, shape, morphology), and mechanical properties (compactibility, tensile strength). These properties can have a direct effect on the ability to process and manufacture the active pharmaceutical ingredient (API) and the drug product. Polymorphism further has pharmacological implications due to altered solid state properties and suitability for a particular formulation. Thus, polymorphism of an API can affect the quality, safety, efficacy and developability of a drug product and is therefore of fundamental importance [D. Giron et al., *J. Therm. Anal. Cal.* (2004) 77:709].

In addition to polymorphic modifications, an API can be crystallized in different salt forms with an appropriate counterion. Similar to polymorphism, salt forms are varying from each other in the degree of solubility and many other physical and chemical factors, as denoted above. As compared to the free acid or free base of the API, an appropriate salt form might provide improved aqueous solubility, dissolution rate, hygroscopicity, chemical stability, melting point, or mechanical properties.

Solvates, also known as pseudopolymorphs, are crystal forms having either stoichiometric or nonstoichiometric amounts of a solvent incorporated in the crystal lattice. If the incorporated solvent is water, the solvate is commonly known as a hydrate.

The compound of formula (I), its manufacture, its pharmacological activity as Lysine Specific Demethylase-1 (LSD1) inhibitor, and its use for the treatment, prevention and/or delay of progression of diseases associated with LSD1 have been described in WO 2013/057322 (A1).

The compound of formula (I) has now been found to be a highly potent active pharmaceutical ingredient (HPAPI). HPAPIs are effective at much smaller dosage levels than traditional APIs. HPAPIs on one hand are beneficial since they allow effective medicines that require lower doses and hence provoke fewer side effects, but on the other hand they lead to new manufacturing challenges. Safety, Health and Environment (SHE) requirements in compliance with regulatory guidelines necessitate segregated high-containment manufacturing with complex needs regarding facility design, equipment selection and manufacturing processes to achieve desired levels of containment, minimized operator exposure, and ensured worker protection and safety. Hence the highly potent nature is a major issue for process development and manufacturing.

The compound of formula (I) as obtained according to the description of WO 2013/057322 (A1) results in tiny needle shaped crystalline particles in polymorphic Form A.

The final reaction step of the process for the manufacture of the compound of formula (I) is the deprotection of the compound of formula (BOC-I), the tert-butyloxycarbonyl (BOC) protected compound of formula (I), using hydrochloric acid in a solvent, followed by filtration of the obtained solid. Reactive precipitation upon cleavage of the BOC-protecting group with excess HCl under conditions as described in Example 5 on page 158 of WO 2013/057322 (A1) yields a slurry of extremely small particles of Form A which are hardly filterable from the reaction mixture, because e.g. the filter gets clogged. In addition, the small particles of Form A are easily getting electrostatically charged. Handling of the particles with metal equipment (such as spatula) is hardly possible.

Such solid state and particle shape is strongly unwanted for HPAPIs making it very difficult to manufacture the compound of formula (I) in a safe and well-contained way.

There is thus a need for new improved processes and for new improved polymorphic forms in alternative, better processable crystal habits.

In addition, the deprotection of the BOC group under conditions as described in Example 5 on page 158 of WO 2013/057322 (A1) may yield genotoxic by-products from the reaction of the hydrochloric acid and the solvent, thus requiring additional purification steps.

It is also known in the art, that di-hydrochloric acid salts of APIs are prone to decomposition to mono-hydrochloric acid salts thereby releasing corrosive hydrochloric acid. In the development of APIs it is thus normally undesirable to develop di-hydrochloric acid salts because of their known lack of stability and corrosiveness. Surprisingly, a stable di-hydrochloric acid salt of the compound of formula (I) has been found, which does not decompose and release corrosive hydrochloric acid.

It has now been surprisingly found, that under certain conditions new solid forms of the compound of formula (I) can be obtained, which are described hereinafter, which have advantageous utilities and properties. They exhibit substantially different and superior physical and physicochemical properties which may be beneficial in various aspects relevant in API and drug product development, e.g. for dissolution of API, stability and shelf life of API and drug product, and/or facilitated routes of manufacturing or purification. In particular, the instant invention provides novel solid forms of the compound of formula (I) with improved processability, improved safety as well as increased stability of the API.

The new solid forms as described herein are distinguishable by analytical methods as known in the art, particularly by X-ray powder diffraction, crystal structure analysis, vibrational spectroscopy, magnetic resonance and mass spectroscopy, calorimetry, thermogravimmetry, dynamic vapor sorption as well as by microscopy.

The new process for the manufacture of the new solid forms of the compound of formula (I) does not produce any genotoxic by-products making additional purification steps of the product superfluous. The obtained product is therefore of higher purity and reduced toxicity and is produced in a cheaper more efficient and more ecological way.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

Any open valency appearing on a carbon, oxygen, sulfur or nitrogen atom in the structures herein indicates the presence of hydrogen, unless indicated otherwise.

The term "$C_{1-7}$ alcohol" denotes a linear or branched saturated hydrocarbon molecule of 1 to 7 carbon atoms, wherein at least one of the hydrogen atoms has been replaced by a hydroxy group. In particular embodiments, the alcohol has 1 to 4 carbon atoms. In particular embodiments one of the hydrogen atoms has been replaced by a hydroxy group. Particular examples of $C_{1-7}$ alcohol include methanol, ethanol, isopropanol or 2-propanol, n-propanol or 1-propanol, n-butanol or 1-butanol, iso-butanol or 2-methylpropan-1-ol, and tert-butanol or 2-methylpropan-2-ol. Most particular example of $C_{1-7}$ alcohol is 1-propanol.

The term "optional" or "optionally" denotes that a subsequently described event or circumstance may but need not occur, and that the description includes instances where the event or circumstance occurs and instances in which it does not.

The term "active pharmaceutical ingredient" (or "API") denotes the compound in a pharmaceutical composition that has a particular biological activity.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

The term "solid form" or "form" is a general term to denote a crystal form and/or amorphous form of a solid material.

The terms "crystal form" and "crystalline form" can be used interchangeably to denote polymorphs and pseudo-polymorphs of a crystalline solid.

The terms "polymorph" and "modification" can be used synonymously to denote one particular crystal structure in which a compound can crystallize. Different polymorphs have different arrangements or conformations of the molecules in the crystal lattice but all share the same elemental composition.

The term "polymorphism" denotes the ability of a compound to form more than one polymorph.

The term "enantiotropy" denotes the relationship between two or more polymorphs of the same substance in which the rank order of thermodynamic stabilities of the polymorphs changes reversibly at a defined temperature.

The term "monotropy" denotes the relationship between two or more crystal forms of the same substance in which the rank order of thermodynamic stabilities of the polymorphs is retained at all temperatures below the melting point. A "metastable" form is a crystal form which does not have the highest rank order of thermodynamic stability.

The terms "solvate" and "pseudo-polymorph" can be used synonymously to denote a crystal having either stoichiometric or nonstoichiometric amounts of a solvent incorporated in the crystal lattice. If the incorporated solvent is water, the solvate formed is a "hydrate". When the incorporated solvent is alcohol, the solvate formed is an "alcoholate".

The term "salt" denotes a material which is composed of two components, an acid and a base with a clearly defined stoichiometric ratio of the two salt formers. Salt crystals are formed by ionic bonding interactions with complete transfer of hydrogen ions between acid and base.

The term "crystal shape" denotes the basic body element(s) (polyhedron(s)) of which a single crystal is built up. The crystal shape is described by the Miller indices of the lattice planes of the polyhedron(s).

The term "crystal habit" denotes the crystal morphology and hence the physical appearance of a solid form. Variations of crystal habit are caused by different growth rates of lattice planes.

The term "equivalent spherical diameter" (or ESD) of a non-spherical object, e.g. an irregularly-shaped particle, is the diameter of a sphere of equivalent volume.

The terms "d50 value" and "mass-median diameter" (or MMD) can be used interchangeably and denote the average particle size by mass, i.e. the average equivalent diameter of a particle, which is defined as the diameter where 50% (w) of the particles of the ensemble have a larger equivalent spherical diameter, and the other 50% (w) have a smaller equivalent spherical diameter.

The term "agglomerate" denotes an assemblage of primary particles which are rigidly joined together as by fusion, sintering or growth. Agglomerates cannot be readily dispersed. The term "agglomeration" denotes a process by which primary particles are joined together to form an agglomerate.

The term "aggregate" denotes an assemblage of primary particles which are loosely attached to each other by contact. Aggregates can be readily dispersed. The term "aggregation" denotes a process by which primary particles are attached to each other to form an aggregate.

The term "amorphous form" denotes a solid material which does not possess a distinguishable crystal lattice and the molecular arrangement of molecules lacks a long-range order. In particular, amorphous denotes a material that does not show a sharp Bragg diffraction peak. Bragg's law describes the diffraction of crystalline material with the equation "2d·sin(theta)=n·lambda", wherein "d" denotes perpendicular distance (in Angstroms) between pairs of adjacent planes in a crystal ("d-spacing"), "theta" denotes the Bragg angle, "lambda" denotes the wavelength and "n" is an integer. When Bragg's law is fulfilled, the reflected beams are in phase and interfere constructively so that Bragg diffraction peaks are observed in the X-ray diffraction pattern. At angles of incidence other than the Bragg angle, reflected beams are out of phase and destructive interference or cancellation occurs. Amorphous material does not satisfy Bragg's law and no sharp Bragg diffraction peaks are observed in the X-ray diffraction pattern. The XRPD pattern of an amorphous material is further characterized by one or more amorphous halos.

The term "XRPD" denotes the analytical method of X-Ray Powder Diffraction. The repeatability of the angular values is in the range of 2Theta ±0.2°, more particularly in the range of 2Theta ±0.1°. The term "approximately" given in combination with an angular value denotes the variance which is in the range of 2Theta ±0.2°, particularly in the range of 2Theta ±0.1°. The relative XRPD peak intensity is dependent upon many factors such as structure factor, temperature factor, crystallinity, polarization factor, multiplicity, and Lorentz factor. Relative intensities may vary considerably from one measurement to another due to preferred orientation effects. According to USP 941 (US Pharmacopoeia, 37th Edition, General Chapter 941), relative intensities between two samples of the same material may vary considerably due to "preferred orientation" effects. Anisotropic materials adopting preferred orientation will lead to anisotropic distribution of properties such as modulus, strength, ductility, toughness, electrical conductivity, thermal expansion, etc., as described e.g. in Kocks U. F. et al. (Texture and Anisotropy: Preferred Orientations in Polycrystals and Their Effect on Materials Properties, Cambridge University Press, 2000). In XRPD but also Raman spectroscopy, preferred orientations cause a change in the intensity distribution. Preferred orientation effects are particularly pronounced with crystalline APIs of relatively large particle size.

The abbreviation "FWHM" denotes the full width at half maximum, which is a width of a peak (e.g. appearing in a spectrum, particularly in an XRPD pattern) at its half height.

The term "sharp Bragg diffraction peak" in connection with X-ray diffraction patterns denotes a peak which is observed if Bragg's law of diffraction is fulfilled. Generally, the FWHM of a sharp Bragg diffraction peak is less than 0.5° 2-theta.

The term "amorphous halo" in connection with X-ray diffraction patterns denotes an approximately bell-shaped diffraction maximum in the X-ray powder diffraction pattern of an amorphous material. The FWHM of an amorphous halo is on principle larger than the FWHM of the peak of crystalline material.

The terms "FTIR" and "IR" denote the analytical method of infrared spectroscopy.

The term "Raman" denotes the analytical method of Raman spectroscopy. The term "approximately" given in combination with Raman shifts denotes the repeatability which is in the range of ±1 $cm^{-1}$.

The term "confocal Raman microspectroscopy" (CRM) refers to an analytical device wherein a Raman spectrometer is coupled to an optical microscope with the ability to spatially filter the sample volume. CRM allows high magnification visualisation of a sample and Raman analysis of a sample volume with dimensions down to 1 μm and below (Dieing T. et al. (Eds.), Confocal Raman Microscopy, Springer, 2011).

The term "SEM" denotes the analytical method of Scanning Electron Microscopy. Scanning Electron Microscopy is using a highly focused electron beam to scan the surface of the sample to be imaged. When the electrons of this beam interact with the sample, they extract some electrons of inner shell (secondary electrons) of the atoms at the surface of the sample. These emitted electrons are detected by the so-called secondary electron detector. Due to its position looking at an angle of 45 degrees to the sample in comparison to the axis of the exciting electron beam, this allows to generate a shadowing effect. This shadow effect contributes to the very high topographic resolution of the electron microscopy images. Electron microscopy also has the advantage of a large depth of view.

The term "solid state purity" or "purity of solid forms" refers to the quantitative phase analysis in which the degree of crystallinity and the amount of other solid forms is determined and quantified using XRPD according to United States Pharmacopoeia General Chapter <941>.

The term "micronization" denotes a process whereby the particle size of a solid material is diminished to a d50 value of less than 10 μm by the aid of a suitable method, such as milling, bashing or grinding.

The term "ambient conditions" denotes conditions as experienced in a standard laboratory, e.g. atmospheric pressure, air, ambient temperature between 18° C. and 28° C., humidity between 30% rH and 80% rH.

The term "hygroscopicity" describes the ability of a solid material to adsorb moisture. The hygroscopicity of a given API is characterized [*European Pharmacopoeia—6th Edition* (2008), Chapter 5.11) by the increase in mass when the relative humidity is raised from 0% rH to 90% rH:
  non-hygroscopic: weight increase Δm<0.2%;
  slightly hygroscopic: weight increase 0.2%≤Δm<2.0%;
  hygroscopic: weight increase 2.0%≤Δm<15.0%;
  very hygroscopic: weight increase Δm≥15.0%;
  a deliquescent: sufficient water is adsorbed to form a liquid.

The term "highly potent active pharmaceutical ingredient" (HPAPI) denotes an active pharmaceutical ingredients exhibiting a potency defined by either:
  a biologically effective dose at or below 150 μg per kg of body weight;
  a therapeutic daily dose at or below 10 mg;
  an occupational exposure limit (OEL) at or below 10 μg per $m^3$ of air (8 h time-weighted average); or
  an acceptable daily exposure (ADE) at or below 100 μg per day (lifetime exposure).

The term "Acceptable Daily Exposure" (ADE) denotes the dose that is unlikely to cause an adverse health event or undesirable physiological effects if an individual is exposed at or below this dose for the maximum expected duration of use of the drug carrying the contaminant or alternatively for lifetime use.

According to the "heat-of-fusion rule" (or "enthalpy-of-fusion rule") by Burger/Ramberger (A. Burger and R. Ramberger, Mikrochim. Acta, 1979, 2, 259-271) the more stable polymorph has the higher melting point and the higher heat of fusion in a monotropic system. If the higher melting polymorph of a compound has the lower enthalpy (heat) of fusion the two polymorphs are enantiotropic. If the lower melting polymorph has the lower entropy (heat) of fusion the two polymorphs are likely to be monotropically related. If the difference in melting points is larger than 30° C., this rule should not be considered.

According to the "density rule" by Burger/Ramberger (A. Burger and R. Ramberger, Mikrochim. Acta, 1979, 2, 259-271) the more stable polymorph has the higher density. In particular the rule states that if a polymorph has a lower density than another polymorph at ambient temperature, then it may be assumed that at absolute zero the form with the lower density is not stable.

The term "Form A" as used herein denotes the crystalline anhydrous polymorphic form A of (trans)-N1-((1R,2S)-2-phenylcyclopropyl)cyclohexane-1,4-diamine di-hydrochloride.

The term "Form B" as used herein denotes the crystalline anhydrous polymorphic form B of (trans)-N1-((1R,2S)-2-phenylcyclopropyl)cyclohexane-1,4-diamine di-hydrochloride.

The term "Form C" as used herein denotes the crystalline anhydrous polymorphic form C of (trans)-N1-((1R,2S)-2-phenylcyclopropyl)cyclohexane-1,4-diamine di-hydrochloride.

DETAILED DESCRIPTION OF THE INVENTION

In detail, the present invention relates novel solid forms, particularly crystalline forms, of a compound of formula (I)

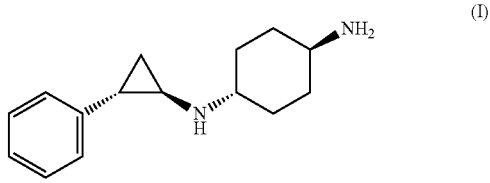 [SMILES: N[C@H]1CC[C@H](N[C@@H]2C[C@H]2c2ccccc2)CC1]

(I)

or salts thereof.

The compound of formula (I) refers to (trans)-N1-((1R,2S)-2-phenylcyclopropyl)cyclohexane-1,4-diamine [CAS Reg. No. 1431304-21-0] and vice versa.

In particular, the compound of formula (I) refers to a hydrochloride salt of (trans)-N1-((1R,2S)-2-phenylcyclopropyl)cyclohexane-1,4-diamine and vice versa.

Most particularly, the compound of formula (I) refers to (trans)-N1-((1R,2S)-2-phenylcyclopropyl)cyclohexane-1,4-diamine di-hydrochloride [CAS Reg. No. 1431303-72-8] and vice versa.

In a particular embodiment of the invention, the solid form of the compound of formula (I) as described above is a crystalline form.

In a particular embodiment of the invention, the solid form of the compound of formula (I) as described above is a di-hydrochloride salt.

In a particular embodiment of the invention, the solid form of the compound of formula (I) as described above is present in the specified solid form in a purity of at least 90% (w/w), particularly at least 95% (w/w), most particularly at least 99% (w/w).

Form A (trans)-N1-((1R,2S)-2-phenylcyclopropyl)cyclohexane-1,4-diamine di-hydrochloride in anhydrous polymorphic form A (Form A) has been implicitly disclosed in WO 2013/057322 (A1).

Form A has been found to occur as small flake-shaped particles as can be seen from the SEM micrographs displayed in FIGS. 11 and 12. Form A has further been found to be slightly hygroscopic. Due to disadvantageous particle size and particle shape, Form A is not optimally suited for drug product development.

Form A is characterized by the XRPD diffraction pattern of FIG. 1.

Form A is characterized by an XRPD diffraction pattern comprising XRPD peaks at peak positions as denoted in Table 2, particularly by XRPD peaks at angles of diffraction 2Theta of 3.4°, 14.6°, 20.3°, 20.6°, 25.0° and 25.6°.

Form A is further characterized by the IR spectrum of FIG. 5.

Form A is further characterized by characteristic bands ($cm^{-1}$) in the IR spectrum as denoted in Table 6.

Form A is further characterized by the Raman spectra of FIGS. 7 and 8.

Form A is further characterized by characteristic bands ($cm^{-1}$) in the Raman spectrum as denoted in Table 8.

It has been found that (trans)-N1-((1R,2S)-2-phenylcyclopropyl)cyclohexane-1,4-diamine di-hydrochloride can be prepared and isolated in other different crystalline modifications, which are distinguishable by their X-ray powder diffraction patterns, vibrational spectra and which exhibit surprising but relevant advantages beneficial for API and drug product development and administration as compared to previously described Form A.

Besides the previously described Form A of (trans)-N1-((1R,2S)-2-phenylcyclopropyl)cyclohexane-1,4-diamine di-hydrochloride, two further polymorphic anhydrous forms (Form B and Form C), were discovered and characterized.

Form B

Form B of (trans)-N1-((1R,2S)-2-phenylcyclopropyl)cyclohexane-1,4-diamine di-hydrochloride can be obtained if prepared under controlled conditions, even without seeding, e.g. according to the processes as described herein.

As compared to Form A, Form B occurs as larger particles of plate shape as can be seen from the SEM micrographs displayed in FIGS. 13 and 14. Stability of Form B is substantially increased as compared to Form A.

Form B is slightly hygroscopic, but no phase-change is observed during long-term incubation at elevated temperature or at elevated humidity, even at 100% rH. Long term storage of Form A at increased humidity, e.g. at 100% rH does not induce a phase change to Form B.

Form B decomposes above 210° C. prior to melting.

Form B has been found to be the most stable polymorph, e.g. in long term equilibration slurry experiments.

One particular embodiment of the invention relates to (trans)-N1-((1R,2S)-2-phenylcyclopropyl)cyclohexane-1,4-diamine di-hydrochloride in anhydrous polymorphic form B (Form B) as described herein.

In a particular embodiment of the invention, Form B is characterized by an XRPD diffraction pattern comprising an XRPD peak at an angle of diffraction 2Theta of 14.9° (±0.1°).

In a particular embodiment of the invention, Form B is characterized by an XRPD diffraction pattern comprising an XRPD peak at an angle of diffraction 2Theta of 14.9° (±0.2°).

In a particular embodiment of the invention, Form B is characterized by an XRPD diffraction pattern comprising an XRPD peak at an angle of diffraction 2Theta of 24.8° (±0.1°).

In a particular embodiment of the invention, Form B is characterized by an XRPD diffraction pattern comprising an XRPD peak at an angle of diffraction 2Theta of 24.8° (±0.2°).

In a particular embodiment of the invention, Form B is characterized by an XRPD diffraction pattern comprising an XRPD peak at an angle of diffraction 2Theta of 16.0° (±0.1°).

In a particular embodiment of the invention, Form B is characterized by an XRPD diffraction pattern comprising an XRPD peak at an angle of diffraction 2Theta of 16.0° (±0.2°).

In a particular embodiment of the invention, Form B is characterized by an XRPD diffraction pattern comprising XRPD peaks at angles of diffraction 2Theta of 14.9° and 24.8° (±0.1°).

In a particular embodiment of the invention, Form B is characterized by an XRPD diffraction pattern comprising XRPD peaks at angles of diffraction 2Theta of 14.9° and 24.8° (±0.2°).

In a particular embodiment of the invention, Form B is characterized by an XRPD diffraction pattern comprising XRPD peaks at angles of diffraction 2Theta of 14.9°, 16.0° and 24.8° (±0.1°).

In a particular embodiment of the invention, Form B is characterized by an XRPD diffraction pattern comprising XRPD peaks at angles of diffraction 2Theta of 14.9°, 16.0° and 24.8° (±0.2°).

In a particular embodiment of the invention, Form B is characterized by an XRPD diffraction pattern comprising XRPD peaks at angles of diffraction 2Theta of 14.9°, 20.6° and 24.8° (±0.1°).

In a particular embodiment of the invention, Form B is characterized by an XRPD diffraction pattern comprising XRPD peaks at angles of diffraction 2Theta of 14.9°, 20.6° and 24.8° (±0.2°).

In a particular embodiment of the invention, Form B is characterized by an XRPD diffraction pattern comprising XRPD peaks at angles of diffraction 2Theta of 14.9°, 16.0°, 20.6° and 24.8° (±0.1°).

In a particular embodiment of the invention, Form B is characterized by an XRPD diffraction pattern comprising XRPD peaks at angles of diffraction 2Theta of 14.9°, 16.0°, 20.6° and 24.8° (±0.2°).

In a particular embodiment of the invention, Form B is characterized by an XRPD diffraction pattern comprising XRPD peaks at angles of diffraction 2Theta of 14.9°, 16.0°, 20.6°, 24.8°, 25.7° and 31.5° (±0.2°).

In a particular embodiment of the invention, Form B is characterized by an XRPD diffraction pattern comprising XRPD peaks at angles of diffraction 2Theta of 14.9°, 16.0°, 20.6°, 24.8°, 25.7° and 31.5° (±0.1°).

In a particular embodiment of the invention, Form B is characterized by an XRPD diffraction pattern comprising XRPD peaks at angles of diffraction 2Theta of 14.9°, 16.0°, 20.6°, 24.8°, 25.7°, 31.5° and 35.9° (±0.2°).

In a particular embodiment of the invention, Form B is characterized by an XRPD diffraction pattern comprising XRPD peaks at angles of diffraction 2Theta of 14.9°, 16.0°, 20.6°, 24.8°, 25.7°, 31.5° and 35.9° (±0.1°).

In a particular embodiment of the invention, Form B is characterized by an XRPD diffraction pattern comprising XRPD peaks at angles of diffraction 2Theta of 14.9°, 16.0°, 20.6°, 24.8°, 25.6° and 31.5° (±0.2°).

In a particular embodiment of the invention, Form B is characterized by an XRPD diffraction pattern comprising XRPD peaks at angles of diffraction 2Theta of 14.9°, 16.0°, 20.6°, 24.8°, 25.6° and 31.5° (±0.1°).

In a particular embodiment of the invention, Form B is characterized by an XRPD diffraction pattern comprising XRPD peaks at angles of diffraction 2Theta of 14.9°, 16.0°, 20.6°, 24.8°, 25.6°, 31.5° and 35.9° (±0.2°).

In a particular embodiment of the invention, Form B is characterized by an XRPD diffraction pattern comprising XRPD peaks at angles of diffraction 2Theta of 14.9°, 16.0°, 20.6°, 24.8°, 25.6°, 31.5° and 35.9° (±0.1°).

In a particular embodiment of the invention, Form B is characterized by an XRPD diffraction pattern comprising XRPD peaks at angles of diffraction 2Theta of 14.9°, 16.0°, 20.6°, 24.8°, 31.5° and 35.9° (±0.2°).

In a particular embodiment of the invention, Form B is characterized by an XRPD diffraction pattern comprising XRPD peaks at angles of diffraction 2Theta of 14.9°, 16.0°, 20.6°, 24.8°, 31.5° and 35.9° (±0.1°).

In a particular embodiment of the invention, Form B is characterized by an XRPD diffraction pattern comprising XRPD peaks at angles of diffraction 2Theta of 14.6°, 14.9°, 16.0°, 17.7°, 20.6°, 21.7°, 24.8°, 25.7°, 31.5° and 35.9° (±0.2°).

In a particular embodiment of the invention, Form B is characterized by an XRPD diffraction pattern comprising XRPD peaks at angles of diffraction 2Theta of 14.6°, 14.9°, 16.0°, 17.7°, 20.6°, 21.7°, 24.8°, 25.7°, 31.5° and 35.9° (±0.1°).

In a particular embodiment of the invention, Form B is characterized by an XRPD diffraction pattern comprising XRPD peaks at angles of diffraction 2Theta of 14.6°, 14.9°, 16.0°, 17.7°, 20.6°, 21.7°, 24.8°, 25.6°, 31.5° and 35.9° (±0.2°).

In a particular embodiment of the invention, Form B is characterized by an XRPD diffraction pattern comprising XRPD peaks at angles of diffraction 2Theta of 14.6°, 14.9°, 16.0°, 17.7°, 20.6°, 21.7°, 24.8°, 25.6°, 31.5° and 35.9° (±0.1°).

In a particular embodiment of the invention, Form B is characterized by an XRPD diffraction pattern comprising XRPD peaks at angles of diffraction 2Theta of 14.6°, 14.9°, 16.0°, 17.7°, 20.6°, 21.7°, 24.8°, 25.7°, 31.5° and 35.2° (±0.2°)

In a particular embodiment of the invention, Form B is characterized by an XRPD diffraction pattern comprising XRPD peaks at angles of diffraction 2Theta of 14.6°, 14.9°, 16.0°, 17.7°, 20.6°, 21.7°, 24.8°, 25.7°, 31.5° and 35.2° (±0.1°).

In a particular embodiment of the invention, Form B is characterized by an XRPD diffraction pattern comprising XRPD peaks at angles of diffraction 2Theta of 14.6°, 14.9°, 16.0°, 17.7°, 20.6°, 21.7°, 24.8°, 25.6°, 31.5° and 35.2° (±0.2°).

In a particular embodiment of the invention, Form B is characterized by an XRPD diffraction pattern comprising XRPD peaks at angles of diffraction 2Theta of 14.6°, 14.9°, 16.0°, 17.7°, 20.6°, 21.7°, 24.8°, 25.6°, 31.5° and 35.2° (±0.1°).

In a particular embodiment of the invention, Form B is characterized by an XRPD diffraction pattern comprising XRPD peaks at angles of diffraction 2Theta of 14.6°, 14.9°, 16.0°, 17.7°, 20.6°, 21.7°, 24.8°, 25.7°, 31.5° and 35.1° (±0.2°).

In a particular embodiment of the invention, Form B is characterized by an XRPD diffraction pattern comprising XRPD peaks at angles of diffraction 2Theta of 14.6°, 14.9°, 16.0°, 17.7°, 20.6°, 21.7°, 24.8°, 25.7°, 31.5° and 35.1° (±0.1°).

In a particular embodiment of the invention, Form B is characterized by an XRPD diffraction pattern comprising XRPD peaks at angles of diffraction 2Theta of 14.6°, 14.9°, 16.0°, 17.7°, 20.6°, 21.7°, 24.8°, 25.6°, 31.5° and 35.1° (±0.2°).

In a particular embodiment of the invention, Form B is characterized by an XRPD diffraction pattern comprising XRPD peaks at angles of diffraction 2Theta of 14.6°, 14.9°, 16.0°, 17.7°, 20.6°, 21.7°, 24.8°, 25.6°, 31.5° and 35.1° (±0.1°).

In a particular embodiment of the invention, Form B is characterized by an XRPD diffraction pattern comprising XRPD peaks at angles of diffraction 2Theta of 14.6°, 14.9°, 16.0°, 17.7°, 18.7°, 19.4°, 20.6°, 21.7°, 24.4°, 24.8°, 25.7°, 31.5°, 35.2° and 35.9° (±0.2°).

In a particular embodiment of the invention, Form B is characterized by an XRPD diffraction pattern comprising XRPD peaks at angles of diffraction 2Theta of 14.6°, 14.9°, 16.0°, 17.7°, 18.7°, 19.4°, 20.6°, 21.7°, 24.4°, 24.8°, 25.7°, 31.5°, 35.2° and 35.9° (±0.1°).

In a particular embodiment of the invention, Form B is characterized by an XRPD diffraction pattern comprising XRPD peaks at angles of diffraction 2Theta of 14.6°, 14.9°, 16.0°, 17.7°, 18.7°, 19.4°, 20.6°, 21.7°, 24.4°, 24.8°, 25.6°, 31.5°, 35.2° and 35.9° (±0.2°).

In a particular embodiment of the invention, Form B is characterized by an XRPD diffraction pattern comprising XRPD peaks at angles of diffraction 2Theta of 14.6°, 14.9°, 16.0°, 17.7°, 18.7°, 19.4°, 20.6°, 21.7°, 24.4°, 24.8°, 25.6°, 31.5°, 35.2° and 35.9° (±0.1°).

In a particular embodiment of the invention, Form B is characterized by an XRPD diffraction pattern comprising XRPD peaks at angles of diffraction 2Theta of 14.6°, 14.9°, 16.0°, 17.7°, 18.7°, 19.4°, 20.6°, 21.7°, 24.4°, 24.8°, 25.7°, 31.5°, 35.1° and 35.9° (±0.2°).

In a particular embodiment of the invention, Form B is characterized by an XRPD diffraction pattern comprising XRPD peaks at angles of diffraction 2Theta of 14.6°, 14.9°, 16.0°, 17.7°, 18.7°, 19.4°, 20.6°, 21.7°, 24.4°, 24.8°, 25.7°, 31.5°, 35.1° and 35.9° (±0.1°).

In a particular embodiment of the invention, Form B is characterized by an XRPD diffraction pattern comprising XRPD peaks at angles of diffraction 2Theta of 14.6°, 14.9°, 16.0°, 17.7°, 18.7°, 19.4°, 20.6°, 21.7°, 24.4°, 24.8°, 25.6°, 31.5°, 35.1° and 35.9° (±0.2°).

In a particular embodiment of the invention, Form B is characterized by an XRPD diffraction pattern comprising XRPD peaks at angles of diffraction 2Theta of 14.6°, 14.9°, 16.0°, 17.7°, 18.7°, 19.4°, 20.6°, 21.7°, 24.4°, 24.8°, 25.6°, 31.5°, 35.1° and 35.9° (±0.1°).

In a particular embodiment of the invention, Form B is characterized by an XRPD diffraction pattern comprising XRPD peaks at angles of diffraction 2Theta of 14.6°, 14.9°, 16.0°, 17.7°, 18.7°, 19.4°, 20.6°, 21.7°, 24.4°, 24.8°, 25.7°, 31.5°, 35.2° and 35.9° (±0.2°).

In a particular embodiment of the invention, Form B is characterized by an XRPD diffraction pattern comprising XRPD peaks at angles of diffraction 2Theta of 14.6°, 14.9°, 16.0°, 17.7°, 18.7°, 19.4°, 20.6°, 21.7°, 24.4°, 24.8°, 25.6°, 31.5°, 35.2° and 35.9° (±0.1°).

In a particular embodiment of the invention, Form B is characterized by an XRPD diffraction pattern comprising XRPD peaks at angles of diffraction 2Theta of 14.6°, 14.9°, 16.0°, 17.7°, 18.7°, 19.4°, 20.6°, 21.7°, 24.4°, 24.8°, 25.7°, 31.5°, 35.1° and 35.9° (±0.2°).

In a particular embodiment of the invention, Form B is characterized by an XRPD diffraction pattern comprising XRPD peaks at angles of diffraction 2Theta of 14.6°, 14.9°, 16.0°, 17.7°, 18.7°, 19.4°, 20.6°, 21.7°, 24.4°, 24.8°, 25.7°, 31.5°, 35.1° and 35.9° (±0.1°).

In a particular embodiment of the invention, Form B is characterized by an XRPD diffraction pattern comprising XRPD peaks at angles of diffraction 2Theta of 14.6°, 14.9°, 16.0°, 17.7°, 18.7°, 19.4°, 20.6°, 21.7°, 24.4°, 24.8°, 25.6°, 31.5°, 35.1° and 35.9° (±0.2°).

In a particular embodiment of the invention, Form B is characterized by an XRPD diffraction pattern comprising XRPD peaks at angles of diffraction 2Theta of 14.6°, 14.9°, 16.0°, 17.7°, 18.7°, 19.4°, 20.6°, 21.7°, 24.4°, 24.8°, 25.6°, 31.5°, 35.1° and 35.9° (±0.1°).

In a particular embodiment of the invention, Form B is characterized by an XRPD diffraction pattern comprising XRPD peaks at peak positions as denoted in Table 4, Table 5, Table 10 and/or Table 11 (±0.2°).

In a particular embodiment of the invention, Form B is characterized by the XRPD diffraction pattern of FIG. 2, FIG. 3, FIG. 15 and/or FIG. 16.

In a particular embodiment of the invention, Form B is characterized by the IR spectrum of FIG. 6.

In a particular embodiment of the invention, Form B is characterized by characteristic bands (cm$^{-1}$) in the IR spectrum as denoted in Table 7.

As described above, the compound of formula (I) is a highly potent active pharmaceutical ingredient (HPAPI). The anticipated daily dose is thus very low, i.e. <1 mg/d. Accordingly, the drug load in a solid form will be very low, e.g. less than 1 mg of API per 100 mg of tablet. Detection of the solid form of the compound of formula (I) in a pharmaceutical composition is thus a major challenge requiring dedicated analytical technologies such as spatially resolved spectrocopy as e.g. confocal Raman microspectroscopy.

In a particular embodiment of the invention, Form B is characterized by a characteristic hand (cm$^{-1}$) in the Raman spectrum at 1225 cm$^{-1}$ (±1 cm$^{-1}$).

In a particular embodiment of the invention, Form B is characterized by characteristic bands (cm$^{-1}$) in the Raman spectrum at 1225 cm$^{-1}$ and 745 cm$^{-1}$ (±1 cm$^{-1}$).

In a particular embodiment of the invention, Form B is characterized by characteristic bands (cm$^{-1}$) in the Raman spectrum at 1225 cm$^{-1}$, 745 cm$^{-1}$, 207 cm$^{-1}$, and 106 cm$^{-1}$ (±1 cm$^{-1}$).

In a particular embodiment of the invention, Form B is characterized by characteristic hands (cm$^{-1}$) in the Raman spectrum as denoted in Table 9.

In a particular embodiment of the invention, Form B is characterized by the Raman spectra of FIGS. 9 and 10.

Form C

Form C of (trans)-N1-((1R,2S)-2-phenylcyclopropyl)cyclohexane-1,4-diamine di-hydrochloride has been found to be an unstable high-temperature polymorph. Upon heating, Form A reversibly transforms into Form C at approx. 140° C. Upon cooling Form C transforms back to Form A at approx. 127° C. Decomposition is observed when the material is heated to 210° C. or more. Form A and Form C are enantiotropically related. Form C cannot be prepared upon heating of Form B.

Form C is characterized by the XRPD diffraction pattern of FIG. 4.

Form C is characterized by an XRPD diffraction pattern comprising XRPD peaks at peak positions as denoted in Table 3, particularly by XRPD peaks at angles of diffraction 2Theta of 3.3°, 14.7°, 20.3°, 21.0° and 24.8°.

In a particular embodiment of the invention, XRPD diffraction patterns were recorded using a Cu K alpha radiation source.

Table 1 lists the relevant crystal structure data of Form B. The lattice constants, unit cell volume and calculated density are based on ambient temperature data. For this purpose the lattice constants obtained from single crystal structure analysis were refined with the experimental ambient conditions XRPD reference patterns using the software TOPAS 4.0, Bruker AXS.

TABLE 1

Single Crystal Structural Data of Form B

| Crystal form | | Form B |
|---|---|---|
| Solid form description | | anhydrate |
| Measuring Temperature | | 100K |
| Crystal system | | Monoclinic |
| Space group | | P2(1) |
| Unit cell dimensions: | a | 5.1542 Å |
| | b | 51.6258 Å |
| | c | 6.1715 Å |
| | α | 90° |
| | β | 100.804° |
| | γ | 90° |
| Cell volume | | 1613.06 Å$^3$ |
| API molecules in unit cell | | 2 |
| Calculated density | | 1.249 g/cm$^3$ |

Tables 2, 3, 4, 5, 10 and 11 list the XRPD peak positions and relative intensities of major XRPD peaks of Forms A, B and C. Since Form B is occurs as larger crystals, preferred orientations can cause a change in the intensity distribution and thus four tables are presented (Table 4, Table 5, Table 10 and Table 11).

Tables 2 and 3: XRPD peak positions and relative intensities of major XRPD peaks of Forms A and C.

TABLE 2

Form A

| 2Theta/° | rel. int./% * |
|---|---|
| 3.4 | 22.07 |
| 6.9 | 12.75 |
| 14.6 | 28.42 |
| 15.2 | 16.29 |
| 15.5 | 10.42 |
| 16.7 | 13.93 |
| 17.1 | 13.96 |
| 17.5 | 18.36 |
| 17.7 | 16.18 |
| 18.5 | 16.97 |
| 19.2 | 12.05 |
| 19.9 | 10.82 |
| 20.3 | 29 |
| 20.6 | 24.6 |

TABLE 2-continued

Form A

| 2Theta/° | rel. int./% * |
|---|---|
| 21.0 | 12.55 |
| 21.4 | 16.52 |
| 21.6 | 16.53 |
| 24.0 | 11.51 |
| 24.4 | 10.08 |
| 25.0 | 100 |
| 25.4 | 11.68 |
| 25.6 | 20.02 |
| 30.9 | 11.39 |
| 31.3 | 18.6 |
| 35.4 | 14.14 |
| 35.7 | 10.77 |

TABLE 3

Form C

| 2Theta/° | rel. int./% * |
|---|---|
| 3.3 | 100 |
| 6.6 | 26.94 |
| 14.1 | 10.16 |
| 14.7 | 42.78 |
| 15.0 | 28.05 |
| 15.6 | 20.97 |
| 16.2 | 23.62 |
| 17.5 | 22.36 |
| 18.3 | 15.57 |
| 18.8 | 15.39 |
| 19.3 | 12.93 |
| 19.9 | 27.89 |
| 20.3 | 54.54 |
| 21.0 | 32.46 |
| 21.4 | 23.15 |
| 21.8 | 16.42 |
| 22.6 | 17.05 |
| 23.5 | 22.75 |
| 24.0 | 18.86 |
| 24.8 | 73.21 |
| 25.6 | 23.03 |
| 26.2 | 10.55 |
| 26.6 | 11.14 |
| 26.9 | 10.36 |
| 29.2 | 12.25 |
| 29.6 | 11.13 |
| 31.2 | 17.6 |
| 35.2 | 18.67 |
| 35.4 | 16.15 |

*Relative intensities may vary considerably from one measurement to another.

Tables 4, 5, 10 and 11: XRPD peak positions and relative intensities of major XRPD peaks of Form B.

TABLE 4

Form B

| 2Theta/° | rel. int./%* |
|---|---|
| 3.4 | 59.9 |
| 6.8 | 22.7 |
| 10.2 | 11.9 |
| 13.6 | 11.4 |
| 14.6 | 23.4 |
| 14.9 | 77.2 |
| 15.4 | 17.6 |
| 16.1 | 49.1 |
| 16.8 | 16.1 |
| 17.5 | 12.5 |

TABLE 4-continued

Form B

| 2Theta/° | rel. int./%* |
|---|---|
| 17.7 | 28.9 |
| 18.1 | 14.2 |
| 18.5 | 10.3 |
| 18.7 | 21.1 |
| 18.9 | 10.4 |
| 19.4 | 20.1 |
| 19.9 | 11.0 |
| 20.2 | 11.3 |
| 20.6 | 69.6 |
| 20.8 | 12.0 |
| 21.1 | 22.2 |
| 21.7 | 35.3 |
| 22.1 | 12.0 |
| 23.0 | 11.2 |
| 23.8 | 30.9 |
| 23.9 | 11.4 |
| 24.4 | 49.1 |
| 24.8 | 100.0 |
| 25.2 | 13.2 |
| 25.7 | 45.5 |
| 27.9 | 10.9 |
| 30.4 | 12.1 |
| 31.2 | 10.4 |
| 31.5 | 31.3 |
| 35.2 | 13.8 |
| 35.6 | 12.7 |
| 35.9 | 19.4 |

TABLE 5

Form B

| 2Theta/° | rel. int./%* |
|---|---|
| 3.4 | 2.9 |
| 14.6 | 11.3 |
| 14.9 | 38.0 |
| 15.4 | 4.0 |
| 16.0 | 8.0 |
| 16.8 | 2.4 |
| 17.5 | 3.9 |
| 17.7 | 13.9 |
| 18.1 | 4.1 |
| 18.7 | 4.7 |
| 19.4 | 2.9 |
| 20.2 | 2.0 |
| 20.6 | 54.0 |
| 20.8 | 3.3 |
| 21.2 | 3.3 |
| 21.6 | 11.0 |
| 23.8 | 2.2 |
| 24.4 | 2.7 |
| 24.8 | 100.0 |
| 25.2 | 3.1 |
| 25.6 | 21.7 |
| 29.3 | 4.2 |
| 29.5 | 3.8 |
| 29.7 | 4.0 |
| 31.3 | 3.1 |
| 31.5 | 22.8 |
| 31.7 | 3.4 |
| 32.0 | 4.5 |
| 35.2 | 10.5 |
| 35.3 | 4.5 |
| 35.6 | 8.8 |
| 35.9 | 8.3 |
| 37.1 | 2.6 |
| 37.2 | 2.6 |

TABLE 10

Form B

| 2Theta/° | rel. int./%* |
|---|---|
| 14.6 | 10.6 |
| 14.9 | 27.8 |
| 15.4 | 3.9 |
| 16.0 | 7.2 |
| 16.8 | 3.2 |
| 17.5 | 4.0 |
| 17.7 | 9.7 |
| 18.1 | 4.5 |
| 18.7 | 5.5 |
| 19.4 | 4.1 |
| 20.6 | 58.0 |
| 20.8 | 3.3 |
| 21.2 | 2.6 |
| 21.6 | 11.9 |
| 24.8 | 100.0 |
| 25.2 | 3.2 |
| 25.6 | 10.2 |
| 29.3 | 4.2 |
| 29.5 | 4.0 |
| 29.7 | 3.7 |
| 31.3 | 3.2 |
| 31.5 | 26.9 |
| 31.7 | 2.8 |
| 32.0 | 3.1 |
| 35.1 | 12.0 |
| 35.3 | 3.8 |
| 35.6 | 8.9 |
| 35.9 | 7.5 |
| 37.0 | 2.9 |
| 37.2 | 3.3 |
| 37.9 | 2.0 |

TABLE 11

Form B

| 2Theta/° | rel. int./%* |
|---|---|
| 3.4 | 5.7 |
| 14.6 | 13.7 |
| 14.9 | 61.3 |
| 15.4 | 7.4 |
| 16.0 | 16.2 |
| 16.8 | 4.4 |
| 17.5 | 4.6 |
| 17.7 | 21.0 |
| 18.1 | 6.9 |
| 18.7 | 8.0 |
| 19.4 | 7.4 |
| 20.6 | 57.0 |
| 20.8 | 4.6 |
| 21.1 | 5.7 |
| 21.6 | 18.2 |
| 23.0 | 3.8 |
| 23.8 | 5.0 |
| 24.4 | 8.9 |
| 24.8 | 100.0 |
| 25.2 | 3.8 |
| 25.7 | 25.2 |
| 29.3 | 4.4 |
| 29.5 | 3.9 |
| 29.7 | 4.9 |
| 30.4 | 2.5 |
| 30.5 | 2.5 |
| 31.3 | 3.1 |
| 31.5 | 22.2 |
| 31.7 | 4.0 |
| 32.0 | 5.3 |
| 35.1 | 12.3 |
| 35.3 | 4.6 |
| 35.6 | 8.8 |

TABLE 11-continued

Form B

| 2Theta/° | rel. int./%* |
|---|---|
| 35.9 | 11.3 |
| 36.6 | 2.5 |
| 37.1 | 3.1 |
| 37.2 | 3.4 |
| 37.9 | 2.6 |

*Relative intensities may vary considerably from one measurement to another.

Table 6 lists the characteristic bands (cm$^{-1}$) in the IR spectrum of Form A (error is ±1 cm$^{-1}$) Underlined peaks with N at the end are due to the Nujol mulling agent.

Table 7 lists the characteristic bands (cm$^{-1}$) in the IR spectrum of Form B (error is ±1 cm$^{-1}$) Underlined peaks with N at the end are due to the Nujol mulling agent.

TABLE 6

Characteristic bands in the IR spectrum of Form A

| Form A Wave-number (cm$^{-1}$) | Intensity (% trans-mission) | Wave-number (cm$^{-1}$) | Intensity (% trans-mission) | Wave-number (cm$^{-1}$) | Intensity (% trans-mission) |
|---|---|---|---|---|---|
| 2924N | 0 | 1500 | 74 | 1047 | 84 |
| 2853N | 4 | 1466 | 30 | 932 | 90 |
| 2692 | 27 | 1392 | 80 | 912 | 86 |
| 2571 | 40 | 1377N | 64 | 881 | 91 |
| 2479 | 56 | 1310 | 89 | 831 | 92 |
| 2434 | 51 | 1208 | 93 | 771 | 92 |
| 2044 | 72 | 1153 | 92 | 752 | 76 |
| 1612 | 58 | 1124 | 87 | 747 | 74 |
| 1531 | 65 | 1111 | 91 | 734 | 86 |
| 1517 | 63 | 1081 | 75 | 691 | 61 |

TABLE 7

Characteristic bands in the IR spectrum of Form B

| Form B Wave-number (cm$^{-1}$) | Intensity (% trans-mission) | Wave-number (cm$^{-1}$) | Intensity (% trans-mission) | Wave-number (cm$^{-1}$) | Intensity (% trans-mission) |
|---|---|---|---|---|---|
| 2924N | 0 | 1530 | 80 | 952 | 86 |
| 2853N | 7 | 1517 | 50 | 935 | 81 |
| 2689 | 21 | 1500 | 76 | 924 | 85 |
| 2656 | 28 | 1466 | 27 | 912 | 77 |
| 2568 | 35 | 1392 | 79 | 881 | 79 |
| 2516 | 53 | 1377N | 69 | 834 | 84 |
| 2476 | 47 | 1208 | 88 | 762 | 72 |
| 2434 | 39 | 1124 | 79 | 756 | 62 |
| 2081 | 85 | 1111 | 82 | 744 | 68 |
| 2045 | 59 | 1080 | 72 | 690 | 48 |
| 1611 | 54 | 1044 | 78 | | |
| 1590 | 72 | 1028 | 85 | | |

Table 8 lists the characteristic bands (cm$^{-1}$) in the Raman spectrum of Form A (error is ±1 cm$^{-1}$) and Table 9 lists the characteristic bands (cm$^{-1}$) in the Raman spectrum of Form B (error is +1 cm$^{-1}$).

TABLE 8

Characteristic bands in the Raman spectrum of Form A

| Form A Wave-number shift (cm$^{-1}$) | Intensity (arb. units) | Wave-number shift (cm$^{-1}$) | Intensity (arb. units) | Wave-number shift (cm$^{-1}$) | Intensity (arb. units) |
|---|---|---|---|---|---|
| 3083 | 0.052 | 1392 | 0.045 | 833 | 0.034 |
| 3055 | 0.155 | 1376 | 0.083 | 790 | 0.144 |
| 3011 | 0.099 | 1311 | 0.046 | 772 | 0.042 |
| 2951 | 0.248 | 1263 | 0.081 | 757 | 0.047 |
| 2934 | 0.155 | 1234 | 0.055 | 734 | 0.034 |
| 2911 | 0.195 | 1220 | 0.071 | 620 | 0.061 |
| 2880 | 0.150 | 1208 | 0.088 | 498 | 0.094 |
| 2868 | 0.149 | 1186 | 0.053 | 449 | 0.054 |
| 2744 | 0.044 | 1159 | 0.040 | 389 | 0.050 |
| 2572 | 0.026 | 1078 | 0.037 | 356 | 0.044 |
| 1606 | 0.145 | 1042 | 0.125 | 281 | 0.043 |
| 1584 | 0.045 | 1003 | 0.206 | 204 | 0.072 |
| 1502 | 0.025 | 956 | 0.028 | 174 | 0.084 |
| 1487 | 0.067 | 933 | 0.034 | 100 | 0.469 |
| 1471 | 0.036 | 915 | 0.038 | 60 | 0.487 |
| 1446 | 0.082 | 882 | 0.037 | | |

TABLE 9

Characteristic bands in the Raman spectrum of Form B

| Form B Wave-number shift (cm$^{-1}$) | Intensity (arb. units) | Wave-number shift (cm$^{-1}$) | Intensity (arb. units) | Wave-number shift (cm$^{-1}$) | Intensity (arb. units) |
|---|---|---|---|---|---|
| 3089 | 0.032 | 1446 | 0.041 | 757 | 0.024 |
| 3069 | 0.053 | 1377 | 0.040 | 745 | 0.026 |
| 3053 | 0.126 | 1312 | 0.024 | 619 | 0.031 |
| 3040 | 0.059 | 1262 | 0.050 | 497 | 0.049 |
| 3013 | 0.072 | 1225 | 0.062 | 477 | 0.039 |
| 2952 | 0.133 | 1209 | 0.042 | 448 | 0.037 |
| 2935 | 0.081 | 1180 | 0.032 | 387 | 0.033 |
| 2910 | 0.099 | 1155 | 0.030 | 277 | 0.030 |
| 2881 | 0.077 | 1073 | 0.025 | 207 | 0.041 |
| 2867 | 0.079 | 1041 | 0.094 | 140 | 0.091 |
| 1606 | 0.095 | 1003 | 0.136 | 106 | 0.240 |
| 1583 | 0.024 | 914 | 0.027 | 77 | 0.299 |
| 1501 | 0.017 | 881 | 0.037 | 58 | 0.384 |
| 1487 | 0.032 | 831 | 0.031 | | |
| 1473 | 0.023 | 791 | 0.068 | | |

The invention further relates to a process for the preparation of solid forms of the compound of formula (I) as defined above comprising the deprotection of the compound of formula BOC-(I) corresponding to tert-butyl ((trans)-4-(((1R,2S)-2-phenylcyclopropyl)amino) cyclohexyl) carbamate, the BOC-protected compound of formula (I).

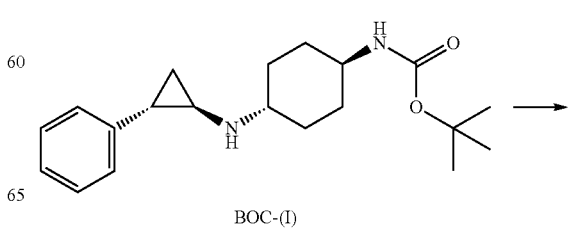

BOC-(I)

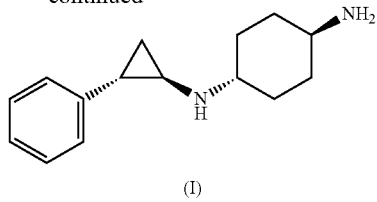

(I)

A further embodiment of the invention relates to a process for the preparation of Form B of the compound of formula (I) as defined above comprising the reaction steps of:

a) Dissolution of a compound of formula BOC-(I) in a solvent;
b) Addition of a solution of HCl;
c) Addition of water at an elevated temperature;
d) Crystallization of the product through gradual decrease of the temperature.

In a particular embodiment of the invention, the solvent in step a) is a $C_{1-7}$ alcohol, particularly 1-propanol.

In a particular embodiment of the invention, step a) is performed at ambient temperature.

In a particular embodiment of the invention, the solution of step b) is an aqueous solution.

In a particular embodiment of the invention, the solution of step b) is an aqueous solution comprising HCl at a concentration of 5% m/m to 40% m/m, more particularly at a concentration of 10% m/m to 35% m/m, most particularly at a concentration of 20% m/m to 30% m/m.

In a particular embodiment of the invention, excess HCl is added in step b).

In a particular embodiment of the invention, 2 to 20 equivalents of HCl are added in step b), more particularly 10 to 15 equivalents of HCl.

In a particular embodiment of the invention, step b) is performed at ambient temperature.

In a particular embodiment of the invention, step b) is followed by agitation, particularly at 30° C. to 50° C., more particularly at 40° C.

In a particular embodiment of the invention, step b) is followed by concentration of the solvent through evaporation.

In a particular embodiment of the invention, at least 5 equivalents of water are added in step c), particularly 10-50 equivalents of water, more particularly 15-20 equivalents of water, most particularly 16-17 equivalents of water.

In a particular embodiment of the invention, water in step c) is added stepwise, particularly dropwise.

In a particular embodiment of the invention, step c) is performed at a temperature above 50° C., particularly at a temperature from 50° C. to 90° C., more particularly from 60° C. to 90° C., even more particularly from 75° C. to 90° C., most particularly from 75° C. to 85° C.

In a particular embodiment of the invention, step c) is followed by agitation of the suspension until dissolution.

In a particular embodiment of the invention, the temperature in step d) is decreased to a final temperature between −20° C. and ambient temperature, particularly to a final temperature between −20° C. and 10° C., most particularly to a final temperature between −10° C. to 0° C.

In a particular embodiment of the invention, the temperature in step d) is decreased at a rate of 1 to 100° C./h, particularly 5 to 20° C./h, most particularly 10° C./h.

In a particular embodiment of the invention, step d) is followed by filtration.

In a particular embodiment of the invention, step d) is followed by filtration and rinsing, particularly by rinsing with the solvent of step a) at a temperature below 0° C.

A further embodiment of the invention relates to a process for the preparation of solid forms of the compound of formula (I) as defined above comprising the reaction steps of:

e) Dissolution of a compound of formula BOC-(I) in 1-propanol;
f) Addition of a solution of HCl in 1-propanol;
g) Physical separation of the precipitate.

In a particular embodiment of the invention, step e) is performed at ambient temperature.

In a particular embodiment of the invention, the solution of step f) comprising HCl at a concentration of 5% m/m to 40% m/m, more particularly at a concentration of 10% m/m to 35% m/m, most particularly at a concentration of 10% m/m to 20% m/m.

In a particular embodiment of the invention, 2 to 20 equivalents of HCl are added in step f), more particularly 10 to 15 equivalents of HCl.

In a particular embodiment of the invention, step f) is performed at ambient temperature.

In a particular embodiment of the invention, step f) is followed by agitation, particularly at 30° C. to 50° C., more particularly at 40° C.

In a particular embodiment of the invention, the physical separation in step g) is a filtration.

In a particular embodiment of the invention, step g) is followed by rinsing with 1-propanol at a temperature below 0° C.

Another embodiment provides pharmaceutical compositions or medicaments comprising solid forms of the compound of formula (I) as described herein, preferably form B as described herein, and a pharmaceutically acceptable excipient, as well as methods of using the solid forms of the compound of formula (I), preferably form B as described herein, to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The solid forms of the compound of formula (I) as described herein may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The solid forms of the compound of formula (I) as described herein may be administered in any convenient administrative form, e.g., tablets, powders, capsules, solutions, dispersions, suspensions, syrups, sprays, suppositories, gels, emulsions, patches, etc. Such compositions may comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a solid form of a compound of formula (I) as described herein and a pharmaceutically acceptable excipient. Suitable excipients are well known to those skilled in the art and are described in detail in, e.g., Ansel H. C. et al., *Ansel's Pharmaceutical Dosage Forms and Drug Delivery Systems* (2004) Lippincott, Williams & Wilkins, Philadelphia; Gennaro A. R. et al., *Remington: The Science and Practice of Pharmacy* (2000) Lippincott, Williams & Wilkins, Philadelphia; and Rowe R. C, *Handbook of Pharmaceutical Excipients* (2005) Pharmaceutical Press, Chicago. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which solid forms of a compound of formula (I) as described herein can be administered can vary within wide limits and will, of course, be fitted to the individual requirements in each particular case.

As described above, the compound of formula (I) is a highly potent active pharmaceutical ingredient (HPAPI). The anticipated daily dose is thus very low, i.e. lower than 10 mg per day. Accordingly, the drug load in a solid form will also be very low, i.e. less than 10 mg of API per 100 mg of tablet.

In general, in the case of oral administration a daily dosage of about 0.01 to 10 mg per person of a solid form of the compound of formula (I) as described herein should be appropriate, although the above upper limit can also be exceeded when necessary.

An example of a suitable oral dosage form is a tablet comprising about 0.01 mg to 10 mg of a solid form of a compound of formula (I) as described herein compounded with about 90 to 30 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving a solid form of a compound of formula (I) as described herein, for example 0.1 to 100 mg, in a suitable buffer solution, e.g. a phosphate buffer, adding a tonicifier, e.g. a salt such as sodium chloride, if desired. The solution may be filtered, e.g., using a 0.2 μm filter, to remove impurities and contaminants.

The solid forms of the compound of formula (I) as described herein, possess valuable pharmacological properties and have been found to be inhibitors of Lysine Specific Demethylase-1 (LSD1). The solid forms of the compound of formula (I) of the present invention can therefore be used, either alone or in combination with other drugs, for the treatment or prevention of diseases which are related to LSD1 or which are modulated by LSD1 inhibitors. These diseases include, but are not limited to cancer, wherein said cancer is chosen from breast cancer, lung cancer, prostate cancer, colorectal cancer, brain cancer, skin cancer, blood cancer, leukemia, lymphoma and myeloma.

In particular, the solid forms of the compound of formula (I) of the present invention can therefore be used, either alone or in combination with other drugs, for the treatment or prevention of blood cancer or lung cancer, more particularly acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), hairy cell leukemia, small cell lung carcinoma (SCLC) and non-small-cell lung carcinoma (NSCLC).

A particular embodiment of the invention also relates to a pharmaceutical composition comprising a solid form of the compound of formula (I) as described herein and at least one pharmaceutically acceptable excipient.

A particular embodiment of the invention also relates to a pharmaceutical composition comprising the compound of formula (I) in Form B as described herein and at least one pharmaceutically acceptable excipient.

A particular embodiment of the invention also relates to a solid form of the compound of formula (I) as described herein, preferably form B as described herein, for use as therapeutically active substances.

A particular embodiment of the invention also relates to a solid form of the compound of formula (I) as described herein preferably form B as described herein, for use in the treatment or prevention of diseases which are related to LSD1 or which are modulated by LSD1 inhibitors.

A particular embodiment of the invention also relates to a solid form of the compound of formula (I) as described herein preferably form B as described herein, for use in the treatment or prevention of cancer, particularly for the treatment or prevention of breast cancer, lung cancer, prostate cancer, colorectal cancer, brain cancer, skin cancer, blood cancer, leukemia, lymphoma and myeloma.

A particular embodiment of the invention embraces solid forms of the compound of formula (I) as described herein preferably form B as described herein, for use in the treatment or prevention of blood cancer or lung cancer, particularly of acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), hairy cell leukemia, small cell lung carcinoma (SCLC) and non-small-cell lung carcinoma (NSCLC).

In another embodiment, the invention relates to a method for the treatment or prevention of diseases which are related to LSD1 or which are modulated by LSD1 inhibitors, which method comprises administering a solid form of the compound of formula (I) as described herein preferably form B as described herein, to a human being or animal.

In another embodiment, the invention relates to a method for the treatment or prevention of cancer, particularly for the treatment or prevention of breast cancer, lung cancer, prostate cancer, colorectal cancer, brain cancer, skin cancer, blood cancer, leukemia, lymphoma and myeloma, which method comprises administering a solid form of the compound of formula (I) as described herein preferably form B as described herein, to a human being or animal.

In a particular embodiment, the invention relates to a method for the treatment or prevention of blood cancer or lung cancer, particularly for the treatment or prevention of acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), hairy cell leukemia, small cell lung carcinoma (SCLC) and non-small-cell lung carcinoma (NSCLC), which method comprises administering a solid form of the compound of formula (I) as described herein preferably form B as described herein, to a human being or animal.

The invention also embraces the use of a solid form of the compound of formula (I) as described herein preferably form B as described herein, for the treatment or prevention of diseases which are related to LSD1 or which are modulated by LSD1 inhibitors.

The invention also embraces the use of a solid form of the compound of formula (I) as described herein preferably form B as described herein, for the treatment or prevention of cancer, particularly for the treatment or prevention of breast cancer, lung cancer, prostate cancer, colorectal cancer, brain cancer, skin cancer, blood cancer, leukemia, lymphoma and myeloma.

The invention also embraces the use of a solid form of the compound of formula (I) as described herein preferably form B as described herein, for the treatment or prevention of blood cancer or lung cancer, particularly for the treatment or prevention of acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), hairy cell leukemia, small cell lung carcinoma (SCLC) and non-small-cell lung carcinoma (NSCLC).

The invention also relates to the use of a solid form of the compound of formula (I) as described herein, preferably form B as described herein, for the preparation of medicaments for the treatment or prevention of diseases which are related to LSD1 or which are modulated by LSD1 inhibitors.

The invention also relates to the use of a solid form of the compound of formula (I) as described herein, preferably form B as described herein, for the preparation of medicaments for the treatment or prevention of cancer, particularly for the treatment or prevention of breast cancer, lung cancer, prostate cancer, colorectal cancer, brain cancer, skin cancer, blood cancer, leukemia, lymphoma and myeloma. Such medicaments comprise a solid form of the compound of formula (I) as described above.

The invention also relates to the use of a solid form of the compound of formula (I) as described herein, preferably form B as described herein, for the preparation of medicaments for the treatment or prevention of blood cancer or lung cancer, particularly for the treatment or prevention of acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), hairy cell leukemia, small cell lung carcinoma (SCLC) and non-small-cell lung carcinoma (NSCLC).

The treatment or prevention of blood cancer is a particular embodiment of present invention.

The treatment or prevention of leukemia, particularly of acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), and hairy cell leukemia are particular embodiments of present invention.

The treatment or prevention of acute myelogenous leukemia (AML) is a particular embodiment of present invention.

The treatment or prevention of lung cancer is a particular embodiment of present invention.

The treatment or prevention of small cell lung carcinoma (SCLC) and non-small-cell lung carcinoma (NSCLC) are particular embodiments of present invention.

The treatment or prevention of small cell lung carcinoma (SCLC) is a particular embodiment of present invention.

DESCRIPTION OF THE DRAWINGS

FIG. 17a shows that Equant crystals are equi-dimensional (like cubes or spheres).
FIG. 17b shows that Plates are flat, tabular crystals and have a similar breath and width; thicker than flakes.
FIG. 17c shows that Flakes are thin, flat crystals that have a similar breadth and width; thinner than plates.
FIG. 17d shows that Blades (laths) are elongated, thin and blade-like crystals.
FIG. 17e shows that Needles are acicular, thin and highly elongated crystals having similar width and breadth.
FIG. 17f shows that Columns are elongated, prismatic crystals with greater width and thickness than needles.

ANALYTICAL METHODS

X-Ray Powder Diffraction

Figure 1:
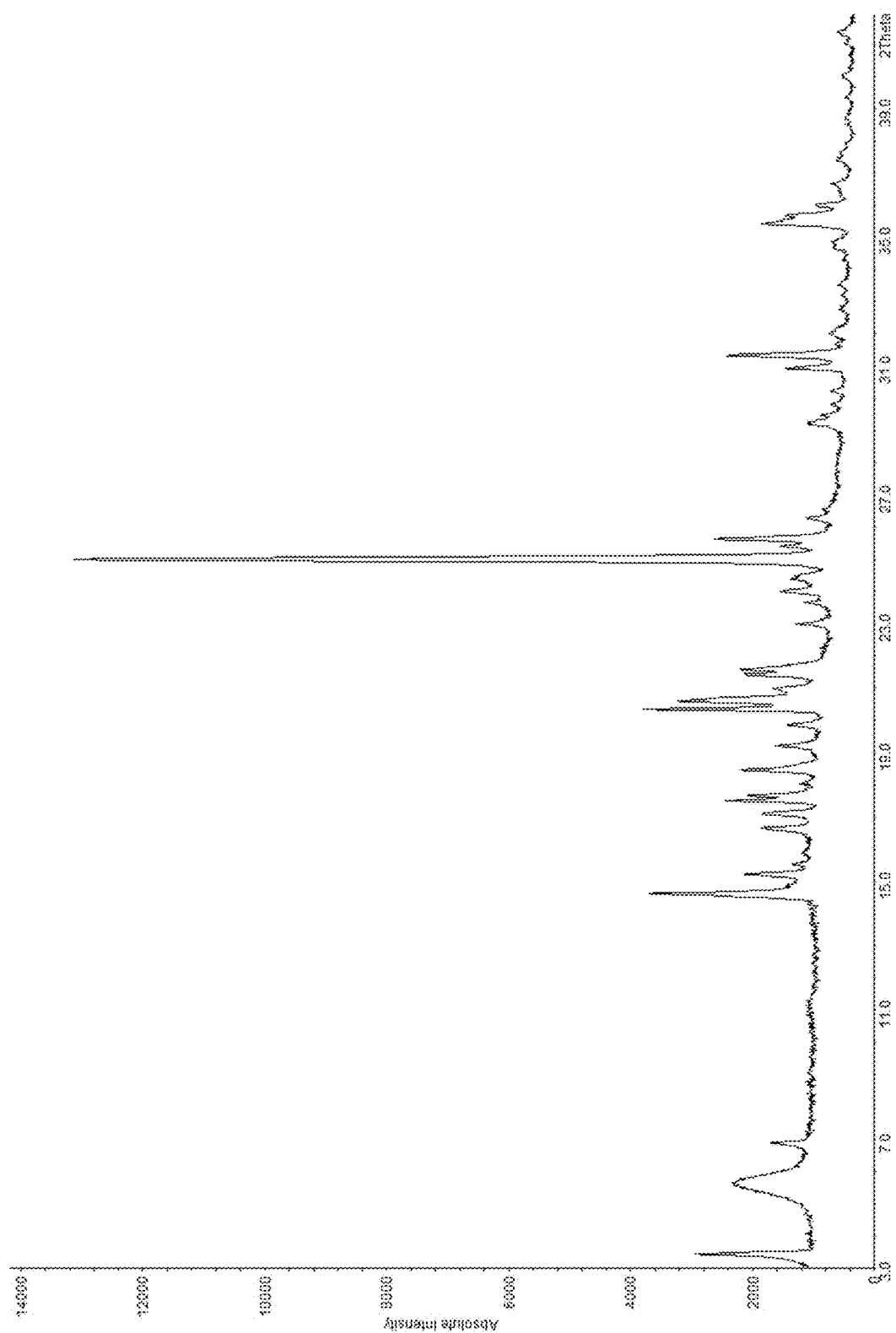
FIG. 1: XRPD pattern of Form A.

XRPD patterns were recorded at ambient conditions in transmission geometry with a STOE STADI P diffractometer (Cu K alpha radiation source, primary Ge-monochromator, position sensitive strip detector (Mythen 1K), angular range 3° to 42° 2Theta, 0.5° 2Theta detector step width, 20 s per step measurement time). The samples were prepared and analyzed without further processing (e.g. grinding or sieving) of the substance.

Temperature Controlled X-Ray Powder Diffraction

For temperature controlled XRPD measurements, the sample was placed without further processing (e.g. grinding or sieving) in a quartz glass capillary of 1 mm diameter and sealed. Measurements were performed with a STOE high-/ low-temperature extension (temperature range −50° C. to 300° C.) with am NiCr/Ni-thermal element at a ramp rate of 5° C. per minute, temperature steps every 5° C., 30 minutes measuring time per step, Single Crystal Structure Analysis For single crystal structure analysis a single crystal sample was mounted in a nylon loop on a goniometer and measured at ambient conditions. Alternatively, the crystal was cooled in a nitrogen stream during measurement. Data were collected on a GEMINI R Ultra diffractometer from Oxford Diffraction. Cu-radiation of 1.54 Å wavelength was used for data collection. Data was processed with the Oxford Diffraction CRYSALIS software. The crystal structure was solved and refined with standard crystallographic software. In this case the program ShelXTL from Bruker AXS (Karlsruhe) was used.

Raman Spectroscopy

The FT-Raman spectra were collected in the spectral range of 4000-50 cm$^{-1}$ with a Bruker MultiRam FT-Raman spectrometer, equipped with a NdYAG 1064 nm laser and a liquid nitrogen cooled Germanium detector. The laser power was about 400 mW, 2 cm$^{-1}$ resolution was used and 2048 scans were co-added. The apodization used was Blackman-Harris 4-term. The samples were run in a glass vial.

The Raman spectra are presented as Raman wavenumber shift (from laser excitation wavenumber) on the x-axis versus arbitrary intensity on the y-axis. The intensity values will vary from instrument to instrument but typically strong Raman peaks will remain strong regardless of which Raman spectrometer used. Peak picking was performed using Thermo Scientific Omnic v8.3.103 (peak position selection set not to contain any decimal places).

Infrared Spectroscopy

The Nujol mull FTIR spectra were collected using a ThermoNicolet 6700 FTIR spectrometer. The sample was prepared as a film of a Nujol suspension consisting of approximately 5 mg of sample and approximately 5 mg of Nujol (mineral oil) between two sodium chloride plates.

The spectral range is between 4000 cm$^{-1}$ and 650 cm$^{-1}$, resolution 2 cm$^{-1}$ and at least 300 co-added scans are collected. Happ-Genzel apodization was used. The spectra were converted to absorbance, after which a linear baseline correction was applied using 10 points. The software used to perform this baseline correction is Thermo Scientific Omnic v8.3.103. Peak picking was also performed using Thermo Scientific Onmic v8.3.103 (peak position selection set not to contain any decimal places).

Scanning Electron Microscopy

The Scanning Electron Microscopy images have been acquired on a Σigma VP (Zeiss, Oberkochen, Germany) system. The secondary electron detector, under high vacuum was used for the image acquisition with an acceleration tension of 3 kV. A line averaging of 17 scans per frame was applied to reduce the noise in the images, resulting in a full acquisition time of 44.6 seconds per image.

In order to allow a good conductivity of the sample, it was prepared by gold sputtering using a Cressington 108 Auto sputter. The parameters were set to 120 seconds of sputtering with a current intensity of 30 mA under a flow of Argon at 0.1 bar.

EXAMPLES

The following examples 1-7 are provided for illustration of the invention. They should not be considered as limiting the scope of the invention, but merely as being representative thereof.

Example 1: Preparation of Crystalline (Trans)-N1-((1R,2S)-2-phenylcyclopropyl) cyclohexane-1,4-diamine di-hydrochloride in anhydrous polymorphic Form A (Form A)

This method of manufacture of Form A corresponds to the procedure as described in example 5 on page 158 of WO 2013/057322 (A1).

Tert-butyl ((trans)-4-(((1R,2S)-2-phenylcyclopropyl)amino)cyclohexyl) carbamate, the BOC-protected compound of formula (I), was obtained as described in step 2 of Example 4 of WO 2013/057322 (A1). To a solution of tert-butyl ((trans)-4-(((1R,2S)-2-phenylcyclopropyl)amino)cyclohexyl) carbamate (160 mg, 0.48 mmol) in 1,4 dioxane (2 mL) at 10° C. added HCl in 1,4 dioxane (2 mL) dropwise and stirred at RT for 16 h. After completion solvent was evaporated, the solid was stirred with diethylether, filtered and dried to afford (trans)-N1-((1R,2S)-2-phenylcyclopropyl)cyclohexane-1,4-diamine di-hydrochloride in Form A (95 mg, 50.8%) as off-white solid.

Example 2: Preparation of Form A

This method of manufacture of Form A corresponds to the alternative procedure as described in example 5 on page 158 of WO 2013/057322 (A1).

To a well stirred solution of (IR, 2S)-2-phenylcyclopropanamine (0.752 g 5.64 mmol) in methanol (10 ml) at room temperature (22-25° C.), molecular sieves (1.0 g) was added followed by t-butyl-4-oxocyclohexylcarbamate (1.07 g, 5.0 mmol) at 10° C. and stirred for 5 min. Acetic acid (0.028 ml, 0.5 mmol) was added at 0-5° C. to the reaction mixture and stirred for 3 h at room temperature. The reaction mixture was cooled to −25 to −30° C., and sodium borohydride (0.229 g, 6.02 mmol) was added portionwise at the same temperature. The reaction mixture was stirred for 3 h allowing the reaction temperature to rise to room temperature.

The progress of the reaction was monitored by thin layer chromatography (TLC) (Ethylacetate (EtOAc)/Hexane 8:2). After completion of reaction, the inorganics were filtered off over celite. The filtrate was evaporated, and the crude residue was taken up in water (20 ml) and dichloromethane (DCM) (20 ml) mixture and basified with 5% aq. NaOH solution (until pH 10). The DCM layer was separated and the aq. layer re-extracted with DCM (20 ml). The combined organic extracts were washed with water (20 ml) and 10% brine solution (20 ml), dried over anhydrous sodium sulfate, filtered and evaporated completely. The crude product was purified by stirring in 2% EtOAc in hexane for 2 h at room temperature to afford t-butyl-4-((1R, 2S)-2-phenylcyclopropylamino)cyclohexylcarbamate as off-white solid (0.90 g, 54%).

To a well stirred solution of t-butyl-4-((1R, 2S)-2-phenylcyclopropylamino) cyclohexylcarbamate, the BOC-protected compound of formula (I), (0.8 g, 2.42 mmol) in 1,4-dioxane (10 ml) at 10-15° C. was slowly added 15% HCl in dioxane (8 ml) and stirred at room temperature for 20 h. The progress of the reaction was monitored by HPLC. After completion of the reaction, the solvent was removed at reduced pressure. The residue was suspended in di-isopropyl ether (15 ml) and stirred for 1 h at room temperature, filtered and dried in vacuo. The crude product was further purified by stirring in di-isopropyl ether (15 ml) for 2 h at room temperature. The solid was filtered off affording (trans)-N1-((1R, 2S)-2-phenylcyclopropyl)cyclohexane-1,4-diamine dihydrochloride in Form A (0.57 g, 77%) (the presence of the dihydrochloride salt form was determined by argentometric titration), as an off white solid.

Example 3: Preparation of Form A

In a 1.5 L double jacket reactor under nitrogen atmosphere at ambient temperature tert-butyl ((trans)-4-(((1R,2S)-2-phenylcyclopropyfiamino)cyclohexyl) carbamate, the BOC-protected compound of formula (I), (50 g, 151 mmol, 1 eq.) was dissolved with 1-propanol (600 g, 750 mL). To the clear solution 11.46%-m/m hydrochloric acid in 1-propanol (289 g, 908 mmol, 6 eq.) was added. The resulting suspension was stirred over night at 40° C.

The product was isolated by filtration and dried over night at 50° C./10 mbar.

Example 4: Preparation of Crystalline (Trans)-N1-((1R,2S)-2-phenylcyclopropyl) cyclohexane-1,4-diamine di-hydrochloride in anhydrous polymorphic Form B (Form B)

5.0 g of tert-butyl ((trans)-4-(((1R,2S)-2-phenylcyclopropyl)amino)cyclohexyl) carbamate, the BOC-protected compound of formula (I), were dissolved in 60 g of 1-propanol at ambient temperature. To this solution 26.5 g of 25%-m/m aqueous HCl (12 eq. of HCl) were added. The resulting white suspension was heated to 40° C. and agitated for 18 h. Then the suspension was heated to 85° C. and 4.5 g of water were added to the white suspension. After approx. 60 min all particles were dissolved. The clear solution was agitated for additional 30 min at 85° C. and then cooled with 10° C./h to −5° C. (within 570 minutes). After agitation at −5° C. for at least 1 h the crystals were isolated by filtration and rinsed with 48 g of cold (−5° C.) 1-propanol. The wet product was dried at 50° C. until weight constant, yielding 3.86 g (84%) Form B as a white powder.

Example 5: Preparation of Form B 0.46 g of Form A were dissolved in 250 mL of water. Air was bubbled through the colorless solution (with a filter frit) for 1 hour at 60° C. by applying vacuum (700-800 mbar). Then, the water was evaporated at 60° C. at 150-50 mbar for 2 hours. Obtained white Form B was dried at 60° C. at 5-8 mbar for 16 hours.

Example 6: Preparation of Form B

Approx. 350 mg of Form A were dissolved in 6 mL of water. The solution was flash-frozen with dry ice and subjected to sublimation for 48 h. Form B was obtained as colorless fluffy powder.

Example 7: Preparation of Crystalline (Trans)-N1-((1R,2S)-2-phenylcyclopropyl) cyclohexane-1,4-diamine di-hydrochloride in anhydrous polymorphic Form C (Form C)

Form C was prepared by heating Form A to approximately 140° C. Below approximately 127° C. re-transformation of Form C into Form A was observed. Above 210° C. decomposition was observed.

The invention claimed is:

1. A solid form of a compound of formula (I) or a salt thereof:

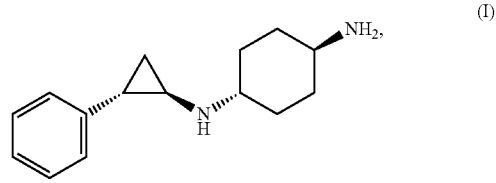 [SMILES: N[C@H]1CC[C@H](N[C@@H]2C[C@H]2c2ccccc2)CC1]

characterized by an XRPD diffraction pattern comprising XRPD peaks at angles of diffraction 2Theta of 14.9°, 16.0° and 24.8° (±0.2°).

2. The solid form according to claim 1, characterized by an XRPD diffraction pattern comprising XRPD peaks at angles of diffraction 2Theta of 14.9°, 16.0°, 20.6°, and 24.8° (±0.2°).

3. The solid form according to claim 1, characterized by an XRPD diffraction pattern comprising XRPD peaks at angles of diffraction 2Theta of 14.9°, 16.0°, 20.6°, 24.8°, 25.7°, and 31.5° (±0.2°).

4. The solid form according to claim 1, characterized by an XRPD diffraction pattern comprising XRPD peaks at angles of diffraction 2Theta of 14.9°, 16.0°, 20.6°, 24.8°, 25.7°, 31.5°, and 35.9° (±0.2°).

5. The solid form according to claim 1, characterized by an XRPD diffraction pattern comprising XRPD peaks at angles of diffraction 2Theta of 14.6°, 14.9°, 16.0°, 17.7°, 18.7°, 19.4°, 20.6°, 21.7°, 24.4°, 24.8°, 25.7°, 31.5°, 35.2°, and 35.9° (±0.2°).

6. The solid form according to claim 1, characterized by the XRPD diffraction pattern comprising XRPD peaks at angles of diffraction 2Theta of 3.4°, 6.8°, 10.2°, 13.6°, 14.6°, 14.9°, 15.4°, 16.1°, 16.8°, 17.5°, 17.7°, 18.1°, 18.5°, 18.7°, 18.9°, 19.4°, 19.9°, 20.2°, 20.6°, 20.8°, 21.1°, 21.7°, 22.1°, 23.0°, 23.8°, 23.9°, 24.4°, 24.8°, 25.2°, 25.7°, 27.9°, 30.4°, 31.2°, 31.5°, 35.2°, 35.6°, and 35.9° (±0.2°).

Figure 2:
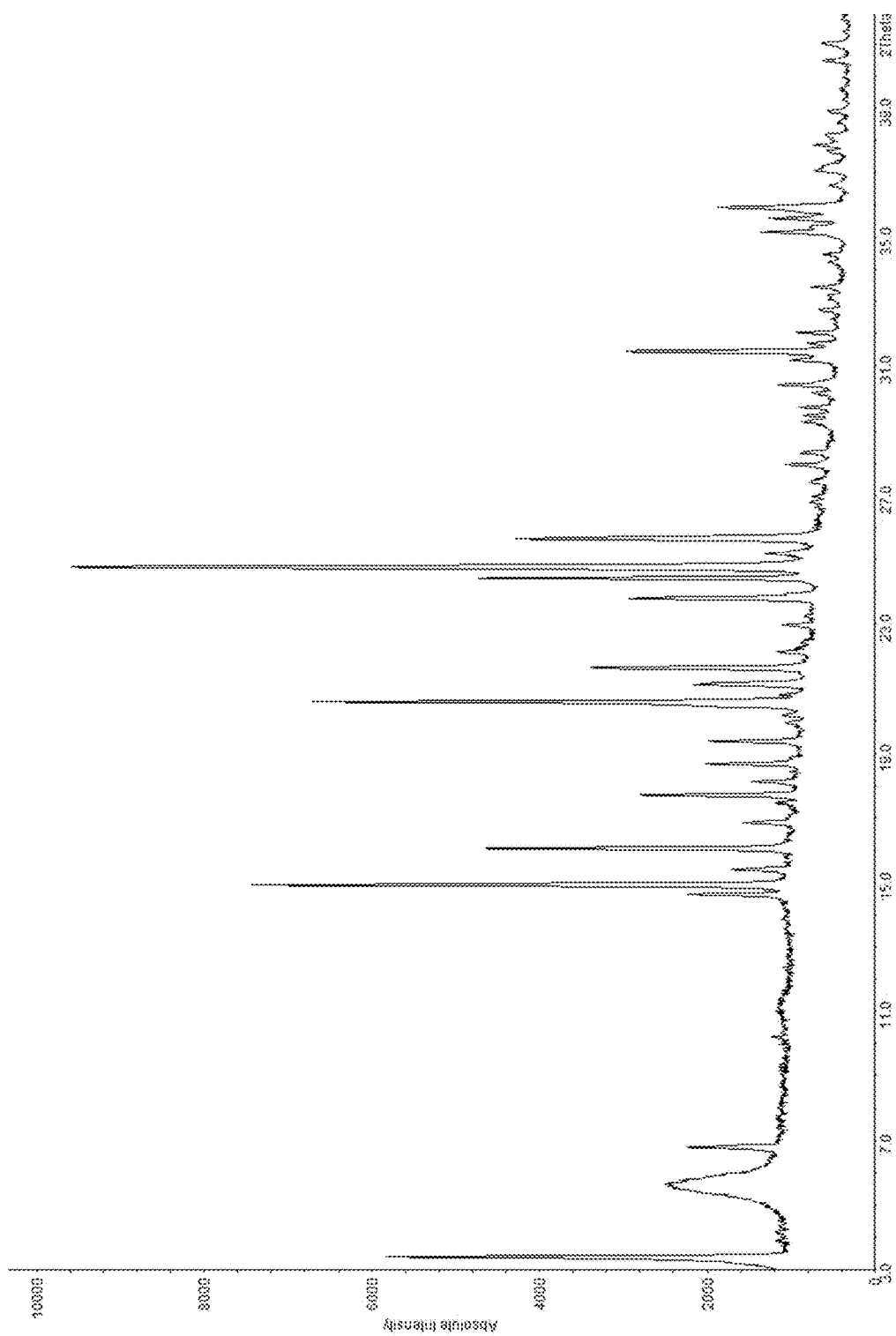
FIG. 2: XRPD pattern of Form B.
Figure 3:
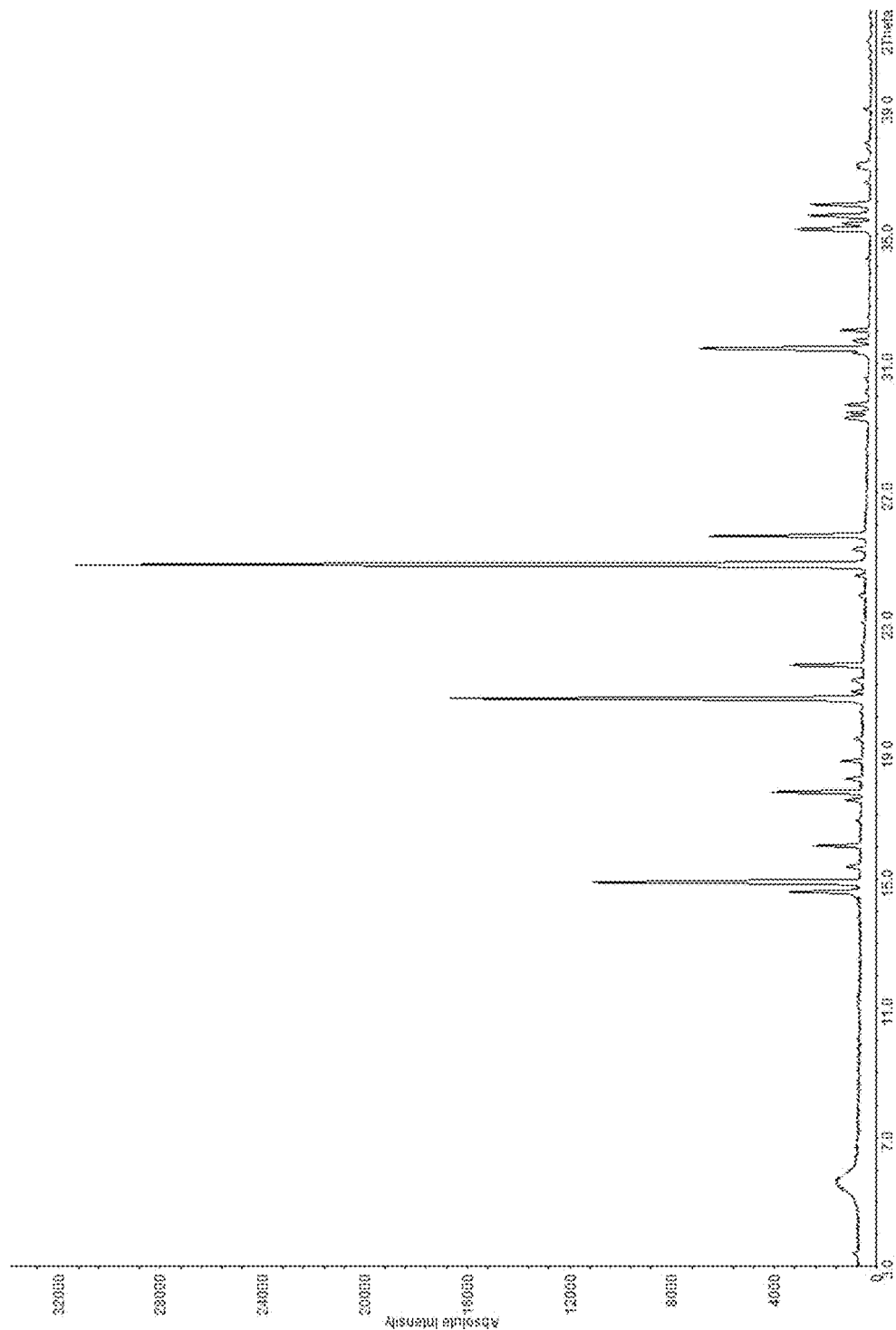
FIG. 3: XRPD pattern of Form B.
Figure 4:
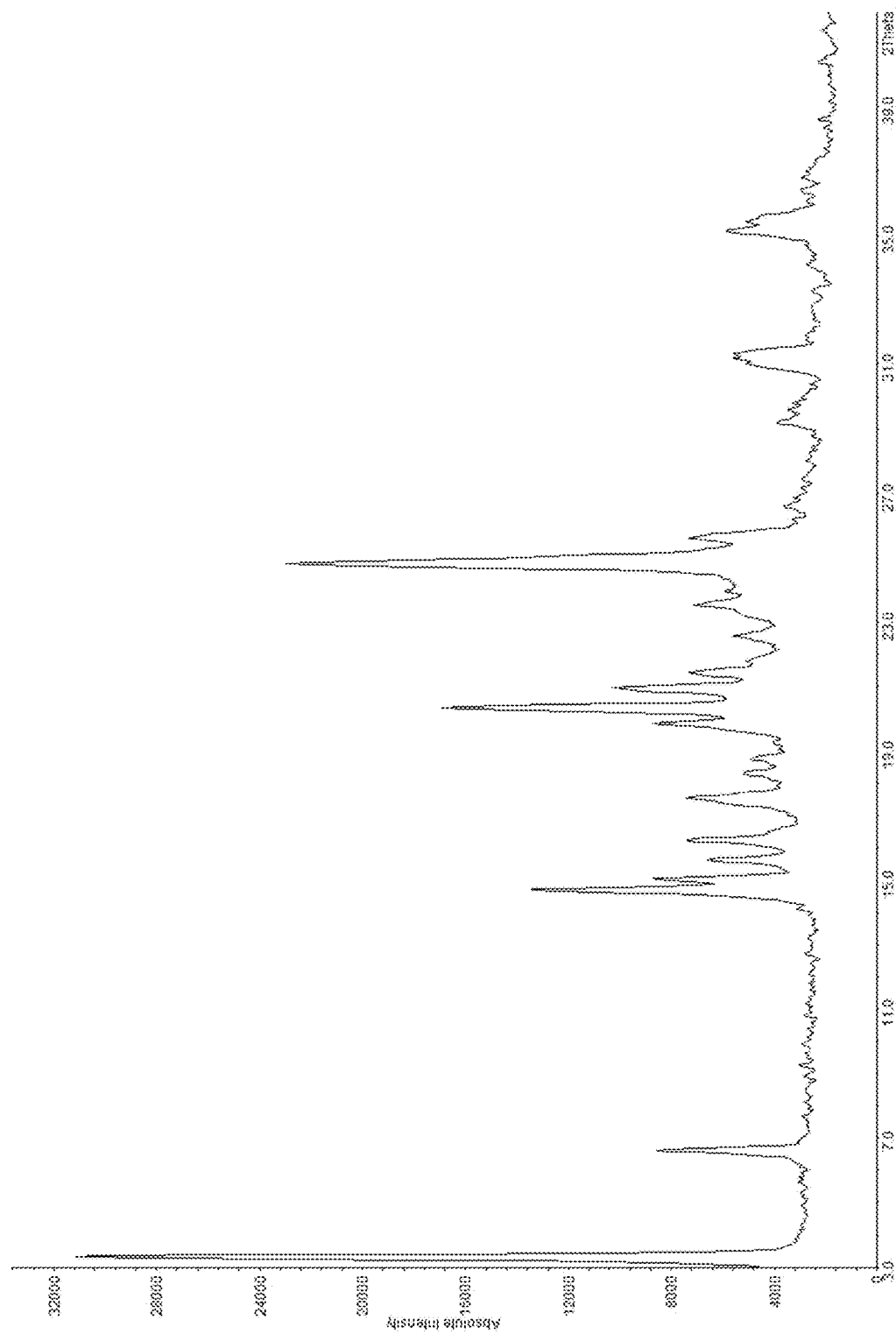
FIG. 4: XRPD pattern of Form C.
Figure 5:
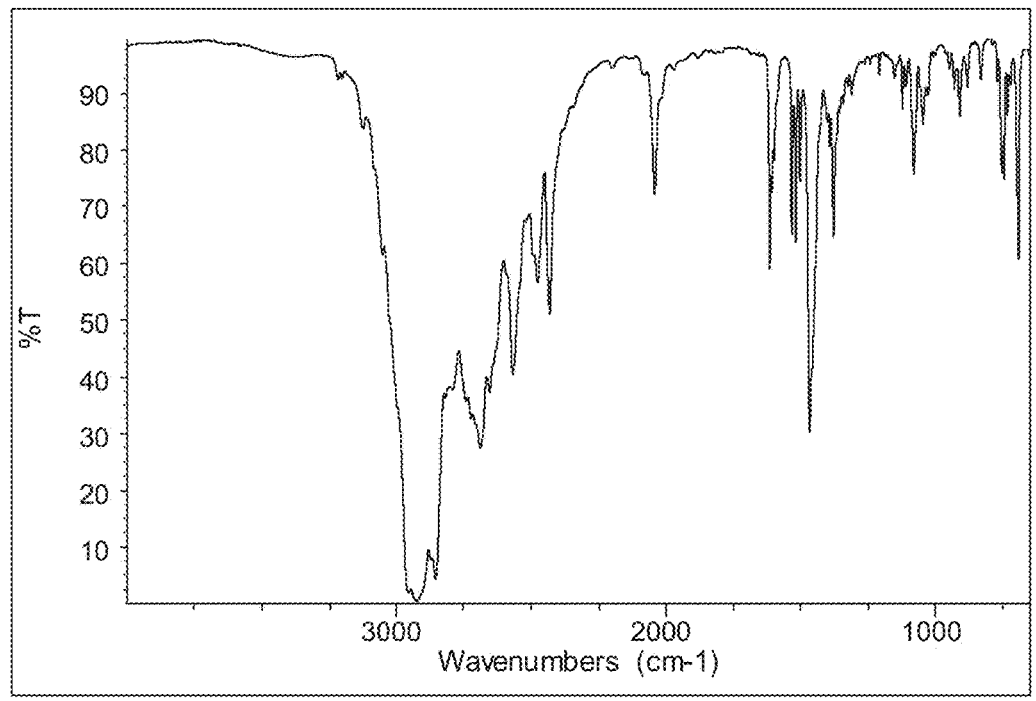
FIG. 5: FTIR Nujol spectrum of Form A.
Figure 6:
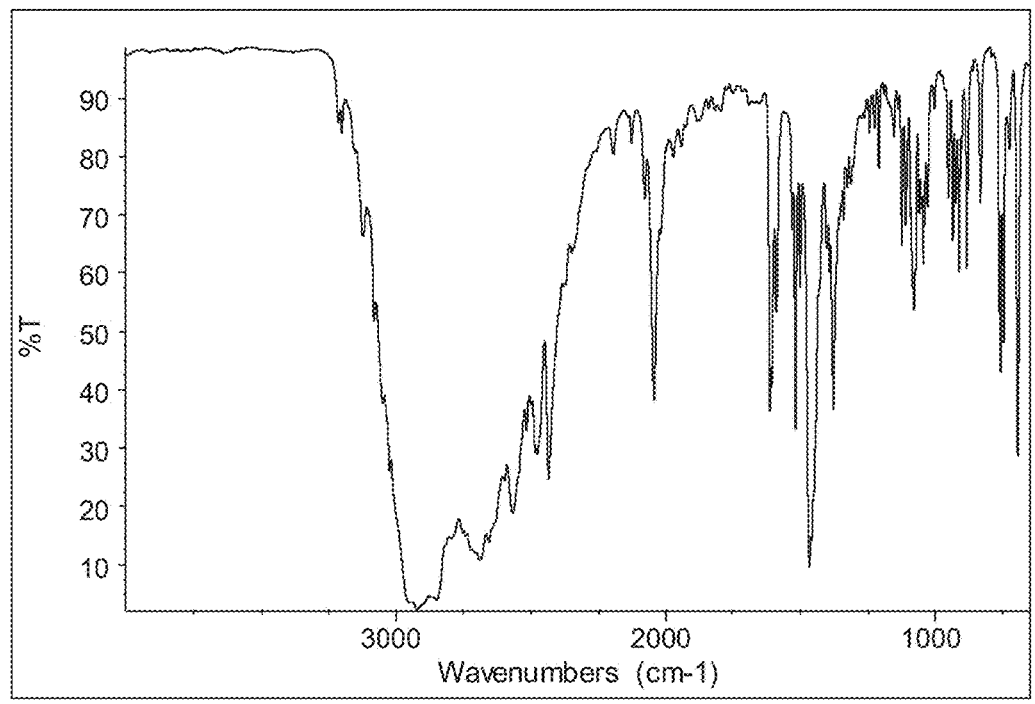
FIG. 6: FTIR Nujol spectrum of Form B.
Figure 7:
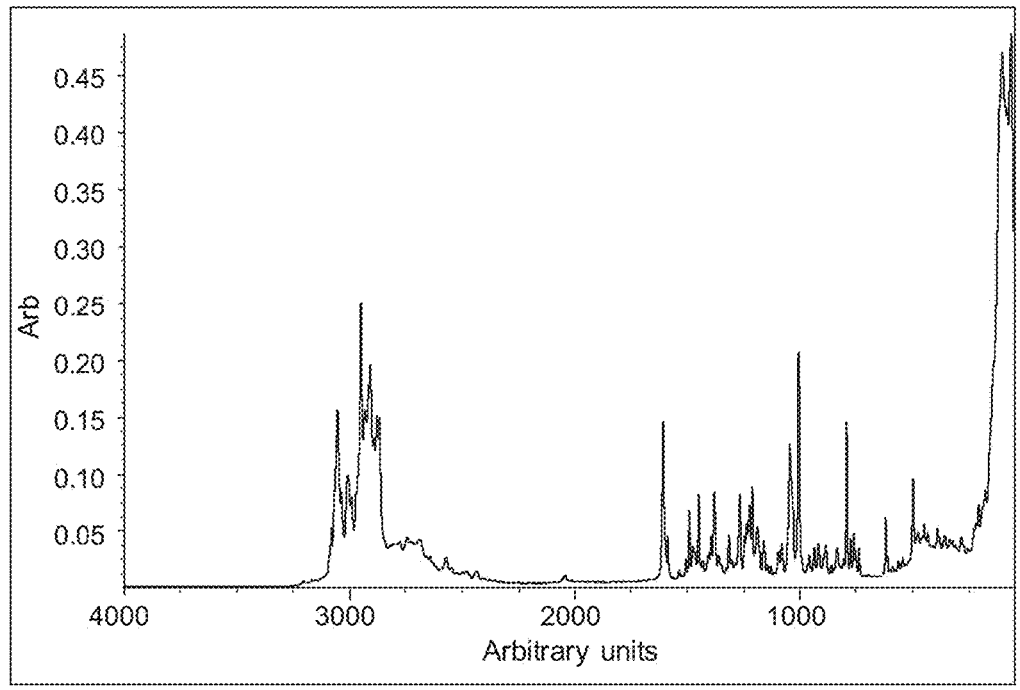
FIG. 7: FT-Raman spectrum of Form A (the units of the x-axis are the Raman wavenumber shift ($cm^{-1}$), the units on the y-axis are arbitrary intensity units).
Figure 8:
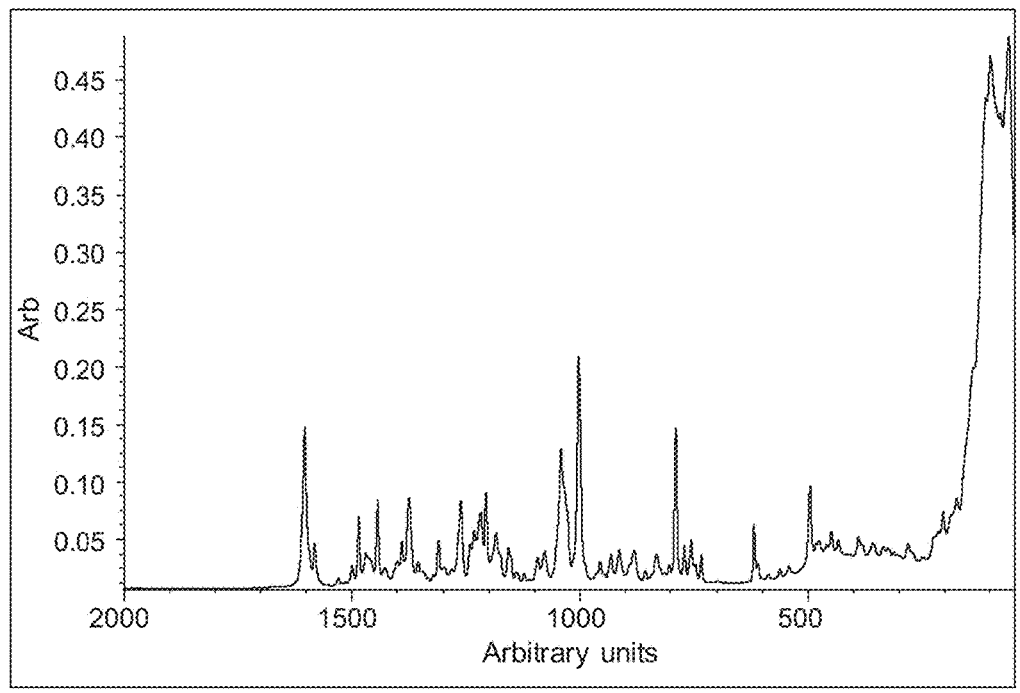
FIG. 8: fingerprint region of FT-Raman spectrum of Form A (the units of the x-axis are the Raman wavenumber shift ($cm^{-1}$), the units on the y-axis are arbitrary intensity units).
Figure 9:
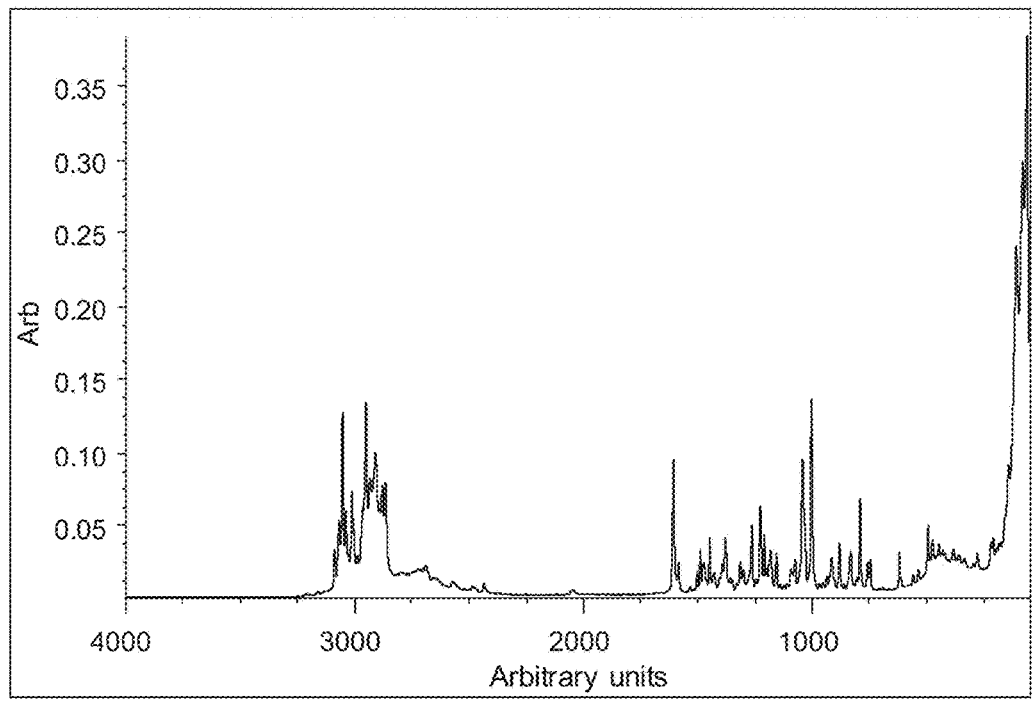
FIG. 9: FT-Raman spectrum of Form B (the units of the x-axis are the Raman wavenumber shift ($cm^{-1}$), the units on the y-axis are arbitrary intensity units).
Figure 10:
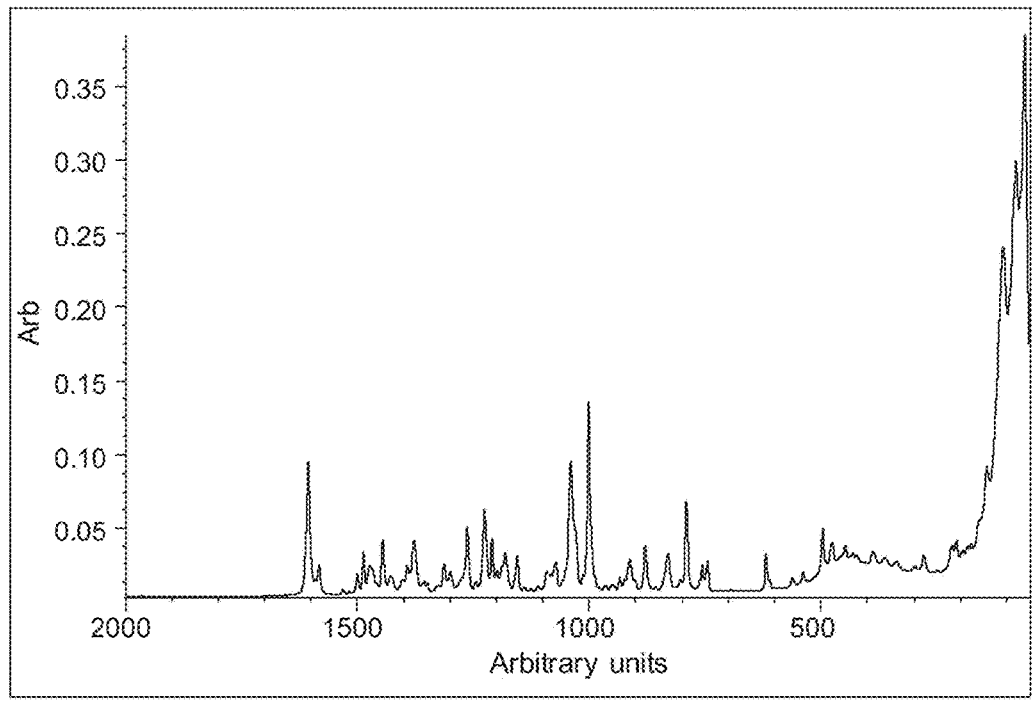
FIG. 10: fingerprint region of FT-Raman spectrum of Form B (the units of the x-axis are the Raman wavenumber shift ($cm^{-1}$), the units on the y-axis are arbitrary intensity units).
Figure 11:
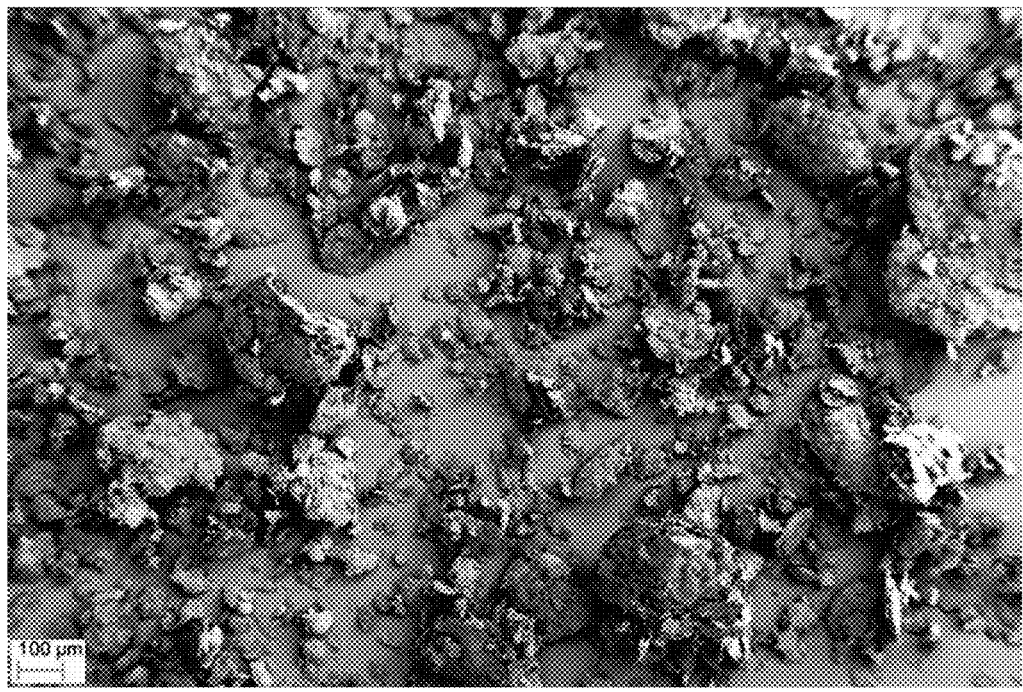
FIG. 11: SEM micrograph of particles of Form A (secondary electron detector, high voltage 3.00 kV, working distance 7.8 mm, magnification 50×).
Figure 12:
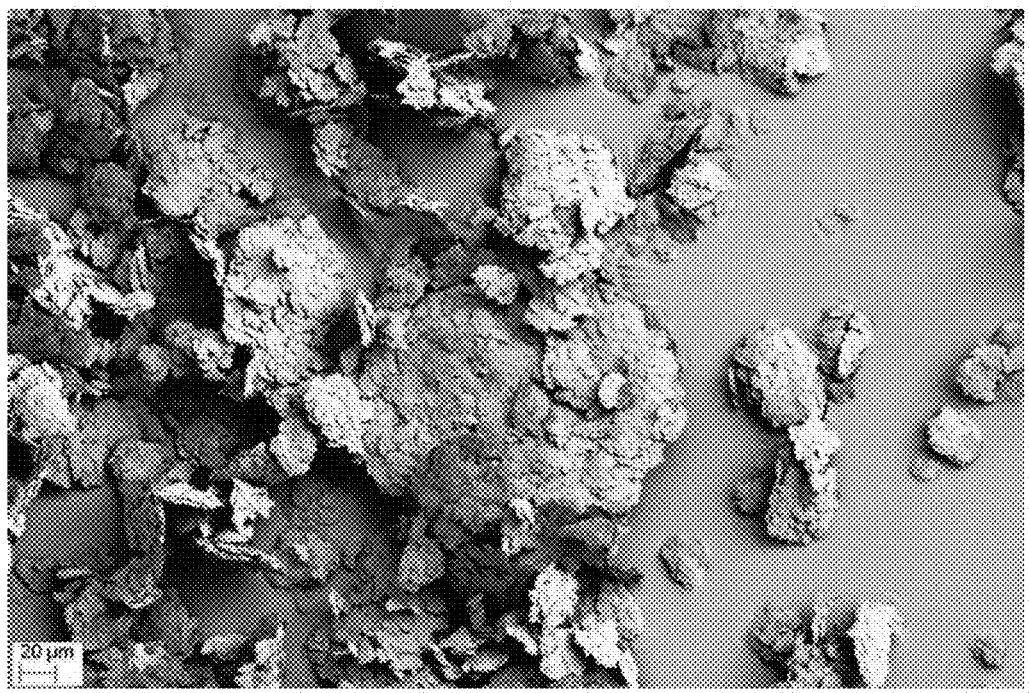
FIG. 12: SEM micrograph of particles of Form A (secondary electron detector, high voltage 3.00 kV, working distance 7.7 mm, magnification 200×).
Figure 13:
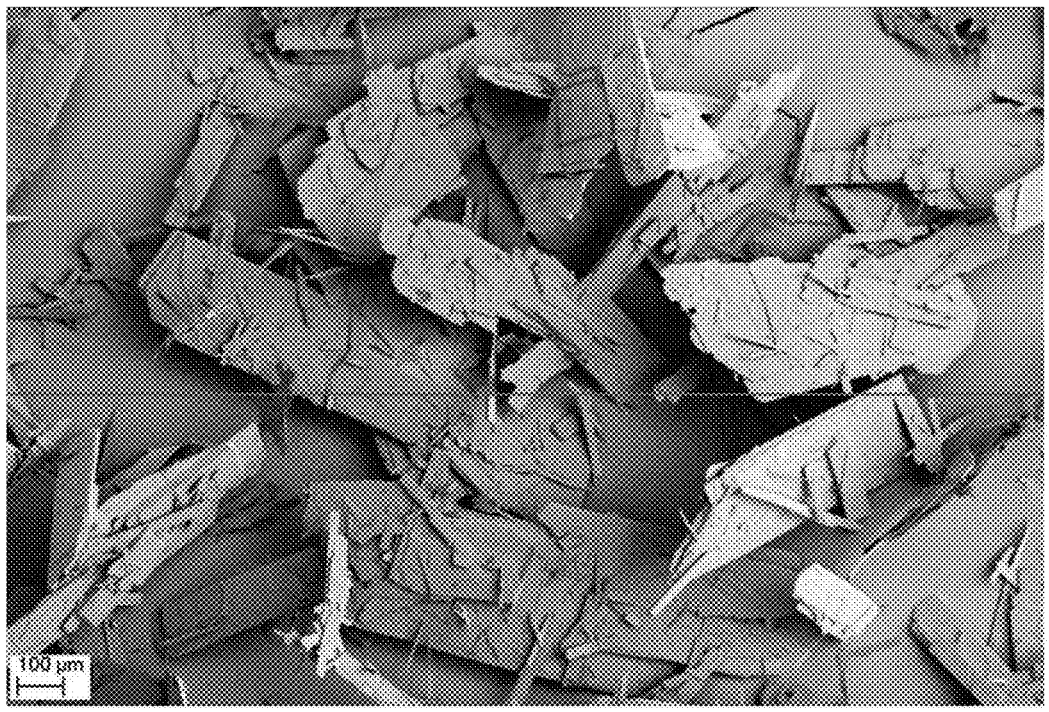
FIG. 13: SEM micrograph of particles of Form B (secondary electron detector, high voltage 3.00 kV, working distance 7.4 mm, magnification 50×).
Figure 14:
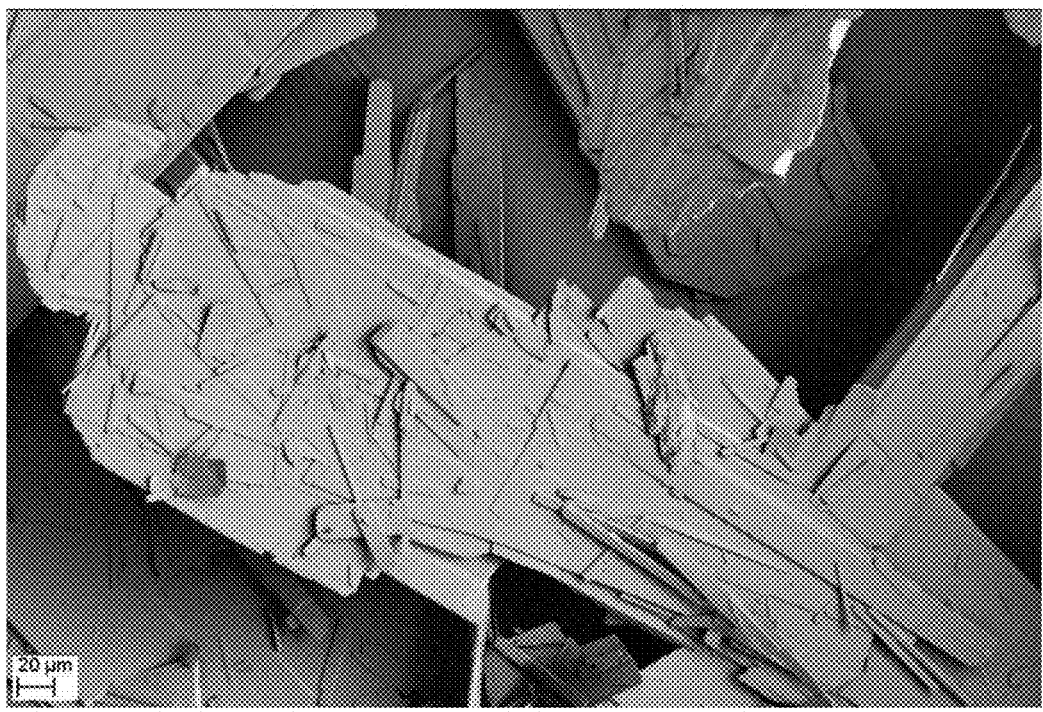
FIG. 14: SEM micrograph of particles of Form B (secondary electron detector, high voltage 3.00 kV, working distance 7.4 mm, magnification 200×).
Figure 15:
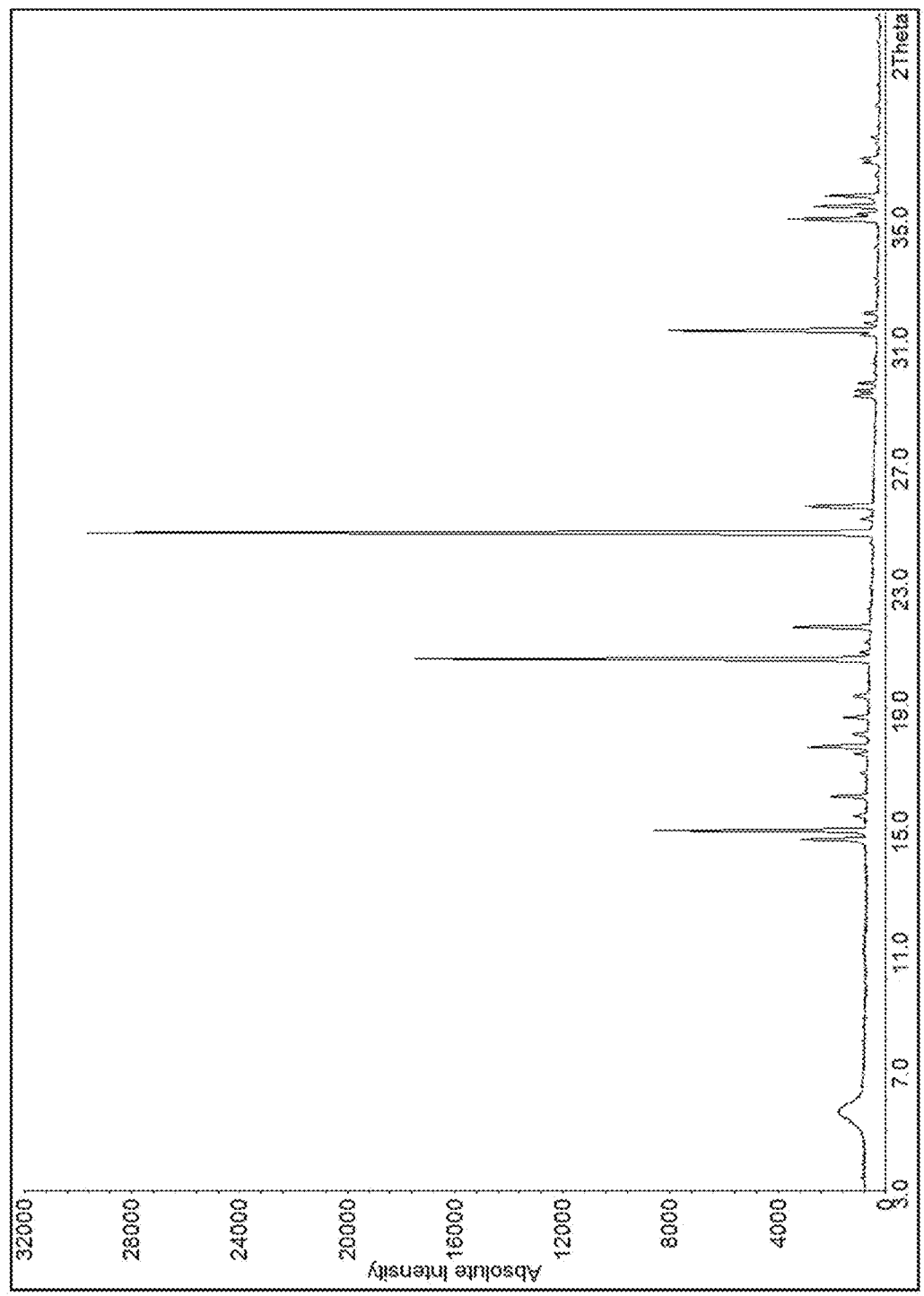
FIG. 15: XRPD pattern of Form B.
Figure 16:
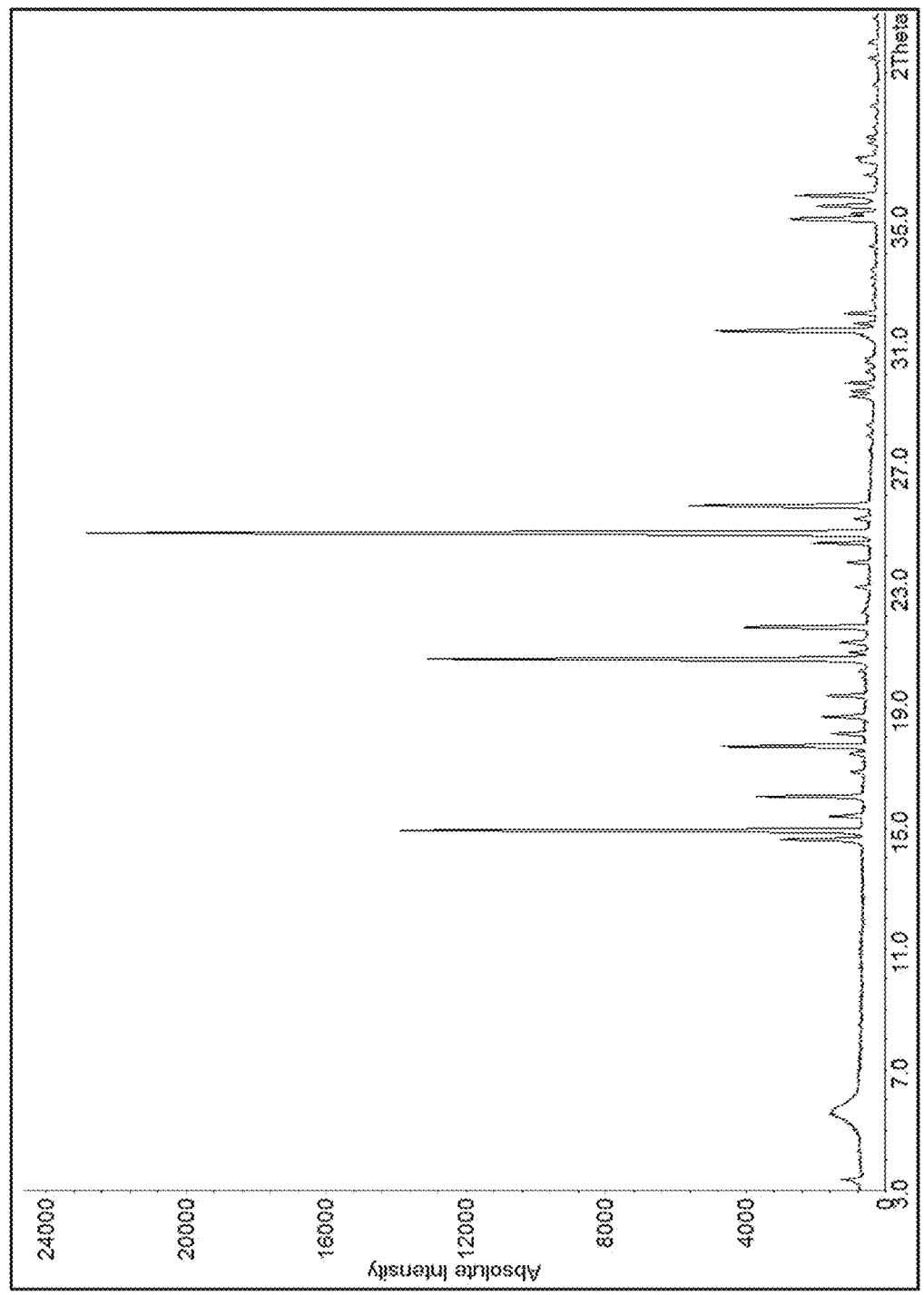
FIG. 16: XRPD pattern of Form B.
Figure 17:
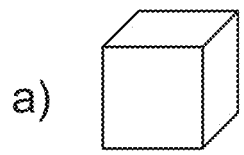
FIG. 17: Crystal habits as distinguished by USP, General Chapter <776> (Optical Microscopy).
Figure 17:
Figure 17:
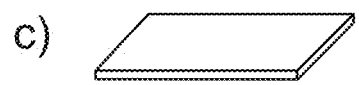
Figure 17:
Figure 17:
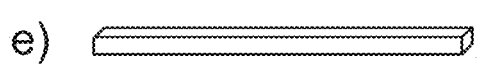
Figure 17:

7. The solid form according to claim 1, characterized by the XRPD diffraction pattern set forth in FIG. 2, FIG. 3, FIG. 15, or FIG. 16.

8. The solid form according to claim 1, characterized by characteristic bands ($cm^{-1}$) in the IR spectrum at 2689 $cm^{-1}$, 2656 $cm^{-1}$, 2568 $cm^{-1}$, 2516 $cm^{-1}$, 2476 $cm^{-1}$, 2434 $cm^{-1}$, 2081 $cm^{-1}$, 2045 $cm^{-1}$, 1611 $cm^{-1}$, 1590 $cm^{-1}$, 1530 $cm^{-1}$, 1517 $cm^{-1}$, 1500 $cm^{-1}$, 1466 $cm^{-1}$, 1392 $cm^{-1}$, 1208 $cm^{-1}$, 1124 $cm^{-1}$, 1111 $cm^{-1}$, 1080 $cm^{-1}$, 1044 $cm^{-1}$, 1028 $cm^{-1}$, 952 $cm^{-1}$, 935 $cm^{-1}$, 924 $cm^{-1}$, 912 $cm^{-1}$, 881 $cm^{-1}$, 834 $cm^{-1}$, 762 $cm^{-1}$, 756 $cm^{-1}$, 744 $cm^{-1}$, and 690 $cm^{-1}$ (±1 $cm^{-1}$).

9. A solid form of a compound of formula (I) or a salt thereof:

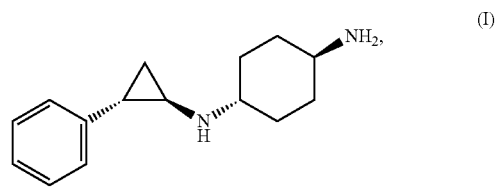 [SMILES: N[C@H]1CC[C@H](N[C@@H]2C[C@H]2c2ccccc2)CC1]

characterized by a band in the Raman spectrum at 1225 $cm^{-1}$ (±1 $cm^{-1}$).

10. The solid form according to claim 1, characterized by a band in the Raman spectrum at 1225 $cm^{-1}$ (±1 $cm^{-1}$).

11. The solid form according to claim 9, characterized by characteristic bands in the Raman spectrum at 1225 $cm^{-1}$ and 745 $cm^{-1}$ (±1 $cm^{-1}$).

12. The solid form according to claim 9, characterized by characteristic bands in the Raman spectrum at 1225 $cm^{-1}$, 745 $cm^{-1}$, 207 $cm^{-1}$, and 106 $cm^{-1}$ (±1 $cm^{-1}$).

13. The solid form according to claim 9, characterized by a Raman spectrum comprising characteristic bands in the Raman spectrum at 3089 $cm^{-1}$, 3069 $cm^{-1}$, 3053 $cm^{-1}$, 3040 $cm^{-1}$, 3013 $cm^{-1}$, 2952 $cm^{-1}$, 2935 $cm^{-1}$, 2910 $cm^{-1}$, 2881 $cm^{-1}$, 2867 $cm^{-1}$, 1606 $cm^{-1}$, 1583 $cm^{-1}$, 1501 $cm^{-1}$, 1487 $cm^{-1}$, 1473 $cm^{-1}$, 1446 $cm^{-1}$, 1377 $cm^{-1}$, 1312 $cm^{-1}$, 1262 $cm^{-1}$, 1225 $cm^{-1}$, 1209 $cm^{-1}$, 1180 $cm^{-1}$, 1155 $cm^{-1}$, 1073 $cm^{-1}$, 1041 $cm^{-1}$, 1003 $cm^{-1}$, 914 $cm^{-1}$, 881 $cm^{-1}$, 831 $cm^{-1}$, 791 $cm^{-1}$, 757 $cm^{-1}$, 745 $cm^{-1}$, 619 $cm^{-1}$, 497 $cm^{-1}$, 477 $cm^{-1}$, 448 $cm^{-1}$, 387 $cm^{-1}$, 277 $cm^{-1}$, 207 $cm^{-1}$, 140 $cm^{-1}$, 106 $cm^{-1}$, 77 $cm^{-1}$, and 58 $cm^{-1}$ (+1 $cm^{-1}$).

14. The solid form according to claim 1, wherein the solid form is present in the specified solid form in a purity of at least 90% (w/w).

15. The solid form according to claim 1, wherein the solid form is a di-hydrochloride salt.

16. A process for the preparation of a solid form according to claim 1 comprising the reaction steps of:
a) dissolution of a compound of formula BOC-(I) in a solvent;

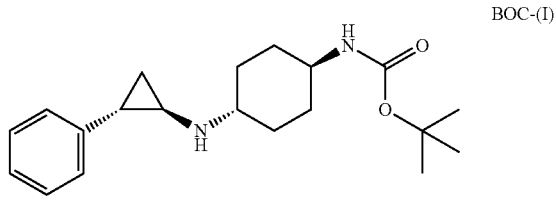 [SMILES: CC(C)(C)OC(=O)N[C@H]1CC[C@H](N[C@@H]2C[C@H]2c2ccccc2)CC1]

BOC-(I)

b) addition of a solution of HCl;
c) addition of water at an elevated temperature; and
d) crystallization of the product through gradual decrease of the temperature.

17. The process according to claim 16, wherein the solvent in step a) is a $C_{1-7}$ alcohol.

18. The process according to claim 16, wherein the solvent in step a) is a 1-propanol.

19. The process according to claim 16, wherein the solution of step b) is an aqueous solution.

20. The process according to claim 16, wherein 2 to 20 equivalents of HCl are added in step b).

21. The process according to claim 16, wherein at least 5 equivalents of water are added in step c).

22. The process according to claim 16, wherein step c) is performed at a temperature above 50° C.

23. The process according to claim 16, wherein the temperature in step d) is decreased to a final temperature between −20° C. and ambient temperature.

24. The process according to claim 16, wherein the temperature in step d) is decreased at a rate of 1 to 100° C./h.

25. A pharmaceutical composition comprising a solid form according to claim 1 and a pharmaceutically acceptable excipient.

26. A method for treating a disease or condition associated with LSD1 or modulated by LSD1 inhibitors, the method comprising administering to an individual in need of such treatment a solid form of a compound according to claim 1.

27. The solid form according to claim 1, characterized by the XRPD diffraction pattern comprising XRPD peaks at angles of diffraction 2Theta of 3.4°, 14.6°, 14.9°, 15.4°, 16.0°, 16.8°, 17.5°, 17.7°, 18.1°, 18.7°, 19.4°, 20.2°, 20.6°, 20.8°, 21.2°, 21.6°, 23.8°, 24.4°, 24.8°, 25.2°, 25.6°, 29.3°, 29.5°, 29.7°, 31.3°, 31.5°, 31.7°, 32.0°, 35.2°, 35.3°, 35.6°, 35.9°, 37.1°, and 37.2° (±0.2°).

28. The solid form according to claim 1, characterized by the XRPD diffraction pattern comprising XRPD peaks at angles of diffraction 2Theta of 14.6°, 14.9°, 15.4°, 16.0°, 16.8°, 17.5°, 17.7°, 18.1°, 18.7°, 19.4°, 20.6°, 20.8°, 21.2°, 21.6°, 24.8°, 25.2°, 25.6°, 29.3°, 29.5°, 29.7°, 31.3°, 31.5°, 31.7°, 32.0°, 35.1°, 35.3°, 35.6°, 35.9°, 37.0°, 37.2° and 37.9° (±0.2°).

29. The solid form according to claim 1, characterized by the XRPD diffraction pattern comprising XRPD peaks at angles of diffraction 2Theta of 3.4°, 14.6°, 14.9°, 15.4°, 16.0°, 16.8°, 17.5°, 17.7°, 18.1°, 18.7°, 19.4°, 20.6°, 20.8°, 21.1°, 21.6°, 23.0°, 23.8°, 24.4°, 24.8°, 25.2°, 25.7°, 29.3°, 29.5°, 29.7°, 30.4°, 30.5°, 31.3°, 31.5°, 31.7°, 32.0°, 35.1°, 35.3°, 35.6°, 35.9°, 36.6°, 37.1°, 37.2° and 37.9° (±0.2°).

30. The solid form according to claim 4, wherein the solid form is a di-hydrochloride salt.

31. The solid form according to claim 9, wherein the solid form is a di-hydrochloride salt.

32. The solid form according to claim 12, wherein the solid form is a di-hydrochloride salt.

33. A pharmaceutical composition comprising a solid form according to claim 9 and a pharmaceutically acceptable excipient.

34. A method for treating a disease or condition associated with LSD1 or modulated by LSD1 inhibitors, the method comprising administering to an individual in need of such treatment a solid form of a compound according to claim 9.

* * * * *